US008022103B2

(12) United States Patent
Xu et al.

(10) Patent No.: US 8,022,103 B2
(45) Date of Patent: Sep. 20, 2011

(54) ESTER PRODRUGS OF PROSTRATIN AND RELATED PHORBOL COMPOUNDS

(75) Inventors: Rensheng Xu, Los Altos, CA (US); Weimin Zhao, Shanghai (CN); Chun Jiang, Belmont, CA (US)

(73) Assignee: Salvia Sciences, Inc., Palo Alto, CA (US)

( * ) Notice: Subject to any disclaimer, the term of this patent is extended or adjusted under 35 U.S.C. 154(b) by 456 days.

(21) Appl. No.: 11/995,527

(22) PCT Filed: Jul. 13, 2006

(86) PCT No.: PCT/US2006/027303
§ 371 (c)(1),
(2), (4) Date: Sep. 22, 2008

(87) PCT Pub. No.: WO2007/009055
PCT Pub. Date: Jan. 18, 2007

(65) Prior Publication Data
US 2009/0163587 A1    Jun. 25, 2009

Related U.S. Application Data

(60) Provisional application No. 60/699,047, filed on Jul. 13, 2005.

(51) Int. Cl.
*A01N 43/20* (2006.01)
*C07D 303/38* (2006.01)
(52) U.S. Cl. ..................................... 514/475; 549/546
(58) Field of Classification Search .................. 514/475; 549/546
See application file for complete search history.

(56) References Cited

U.S. PATENT DOCUMENTS

| | | | |
|---|---|---|---|
| 5,021,450 A | 6/1991 | Blumberg | |
| 5,145,842 A | 9/1992 | Driedger et al. | |
| 5,232,684 A | 8/1993 | Blumberg et al. | |
| 5,405,875 A | 4/1995 | Blumberg et al. | |
| 5,420,162 A | 5/1995 | Blumberg et al. | |
| 5,599,839 A | 2/1997 | Boyd et al. | |
| 5,643,948 A | 7/1997 | Driedger et al. | |
| 5,663,335 A | 9/1997 | Qi et al. | |
| 5,674,902 A | 10/1997 | Blumberg et al. | |
| 5,955,501 A | 9/1999 | Driedger et al. | |
| 5,962,498 A | 10/1999 | Driedger et al. | |
| 6,063,814 A | 5/2000 | Chang et al. | |
| 6,080,784 A | 6/2000 | Driedger et al. | |
| 6,268,395 B1 | 7/2001 | Hattori | |
| 2005/0026902 A1 | 2/2005 | Maziasz | |

FOREIGN PATENT DOCUMENTS

| | | |
|---|---|---|
| CN | 1300592 A | 6/2001 |
| WO | WO 90/15055 A1 | 12/1990 |
| WO | WO 91/18595 A1 | 12/1991 |
| WO | WO 92/02484 A1 | 2/1992 |
| WO | WO 92/17064 A2 | 10/1992 |
| WO | WO 94/27593 A1 | 12/1994 |
| WO | WO 96/40614 A1 | 12/1996 |
| WO | WO 98/46218 A1 | 10/1998 |
| WO | WO 03/037309 A2 | 5/2003 |

OTHER PUBLICATIONS

Vippagunta et al (Adv Drug Deliv Rev 48:3-26, 2001).*
Sigma catalog (1997), 2 pages.*
ARA News, 2001, "AIDS Research Alliance of America Announces Landmark Agreement to Share Drug Profits with Samoan Village Healers," Prostratin Press Release.
Biancotto et al., 2004, "Dual Role of Prostratin in Inhibition of Infection and Reactivation of Human Immunodeficiency Virus from Latency in Primary Blood Lymphocytes and Lymphoid Tissue," *J. Virol.* 78(19):10507-10515.
Bocklandt et al., 2003, "Activation of Latent HIV-1 Expression by the Potent Anti-tumor Promoter 12-deoxyphorbol13-phenylacetate," *Antiviral Res.* 59:89-98.
Brooks et al., 2003, "Molecular Characterization, Reactivation, and Depletion of Latent HIV," *Immunity* 19:413-423.
Chavez et al., 1982, "Four New 12-deoxyphorbol Diesters from Croton Californicus," *J. Natural Products* 45(6):745-8.
Cox et al, 1993, "Saving the Ethnopharmacological Heritage of Samoa," *J. Ethnopharmacol.* 38(2-3):181-188.
Cox et al 1994, "The Ethnobotanical Approach to Drug Discovery: Strengths and Limitations, " *Ciba Found. Symp.* 185:25-36.
Davies et al., 1991, "Induction of Epstein-Barr Virus Lytic Cycle by Tumor-Promoting and Non-Tumor-Promoting Phorbol Esters Requires Active Protein Kinase C ." *J. Virol.* 65:6838-6844.
Erickson et al., 1995, "A Novel Phorbol Ester from *Excoecaria agallocha*," *J. Natural Products* 58(5):769-772.
Fatope et al., 1996, "Selectively Cytotoxic Diterpenes from *Euphorbia poisonii*," *J Med Chem.* 39(4):1005-1008.
Fleisher, D et al., 1996, "Improved Oral Drug Delivery: Solubility Limitations Overcome by the Use of Prodrugs, " *Advanced Drug Delivery Reviews*, 19: 115-130.
Fujiwara et al., 1996, "Mechanism of Selective Inhibition of Human Immunodeficiency Virus by Ingenol Triacetate," *Antimicrob Agents Chemother.* 40(1):271-273.
Fujiwara et al., 1998, "Upregulation of HIV-1 Replication on Chronically Infected Cells by Ingenol Derivatives," *Arch Virol.* 143(10):2003-2010.
Green et al., 1988, "Home Treatment of Skin Cancer and Solar Keratoses," *Australian J Dermatol* 29:127-130.
Gustafson et al, 1992, "A Nonpromoting Phorbol from the Samoan Medicinal Plant Homalanthus Nutans Inhibits Cell Killing by HIV-1," *J. Med. Chem.* 35(11):1978-1986.
Hezareh et al., "Mechanisms of HIV Receptor and Co-receptor Down-regulation by Prostratin: Role of Conventional and Novel PKC Isoforms," *Antiviral Chem. & Chemotherapy* 15:207-222.
International Search Report for PCT/US2006/027303 mailed on Jan. 12, 2007.

(Continued)

*Primary Examiner* — Brandon Fetterolf
*Assistant Examiner* — Shirley V Gembeh
(74) *Attorney, Agent, or Firm* — Virtual Law Partners LLP; Euk Charlie Oh

(57) ABSTRACT

Ester prodrugs of phorbol compounds for the treatment of viral infections, neoplastic diseases, inflammatory reactions, and use as analgesics, wherein the phorbol compounds are derivatized with a -x-o-c(o)-R' group linked to the 6-carbon of the phorbol residue.

40 Claims, No Drawings

OTHER PUBLICATIONS

Korin et al., 2002, "Effects of Prostratin on T-Cell Activation and Human Immunodeficiency Virus Latency," *J Virol.* 76(16):8118-8123.

Kulkosky et al., 2004, "Expression of Latent HAART-Persistent HIV Type 1 Induced by Novel Cellular Activating Agents," *AIDS Research Human Retroviruses* 20(5):497-505.

Kulkosky et al., 2001, "Prostratin: Activation of Latent HIV-1 Expression Suggests a Potential Inductive Adjuvant Therapy for HAART," *Blood.* 98(10):3006-3015.

Lin et al., 2005, "Activation of Human T Cell Leukemia Virus type 1 LTR Promoter and Cellular Promoter Elements by T Cell Receptor Signaling and HTLV-1 Tax Expression" *Virology.* Aug. 15;339(1):1-11.

Liu et al., 1996, "12-Deoxyphorbol Esters from *Euphorbia fischeriana*," *Chinese Chemical Letters* 7(10):917-918.

Ma et al., 1997, "Diterpenoids from *Euphorbia fischeriana*," *Phytochemisty* 44(4), 663-666.

Magar et al., 1992, "Synthesis of Phorbol C-Ring Analogs: A Biomimetic Model Study on the Phorbol to 12-Hydroxydaphnetoxin Conversion," *Org. Chem.* 57(20):5360-5369.

Ogura et al., 1978, "Potential Anticancer Agents VIII," *Planta medica* 33(2):128-43.

Rizk et al., 1985, "Biologically Active Diterpene Esters From *Euphorbia peplus*," *Phytochemistry* 24:1605-6).

Ron et al., 1999, "New Insights into the Regulation of Protein Kinase C and Novel Phorbol Ester Receptors," *The FASEB J.* 13:1658-1676.

Rullas et al., 2004, "Prostratin Induces HN Activation and Downregulates HN Receptors in Peripheral Blood Lymphocytes," *Antiviral Therapy* 9:545-554.

Siliciano et al., 2004, "A Long-term Latent Reservoir for HIV-1: Discovery and Clinical Implications," *J. Antimicrobial Chemo.* 54:6-9.

Silinsky et al., 2003, "Phorbol Esters and Neurotransmitter Release: More than just Protein Kinase C?," *Br J Pharmacol.* 138(7):1191-1201.

Weedon et al., 1976, "Home Treatment of Basal Cell Carcinoma," *Med J of Australia* 1:928.

Wender et al., 1987, "Studies on Tumor Promoters. The First Synthesis of the Phorbol Skeleton," *J. Am. Chem. Soc.* 109:4390-4392.

Williams et al. 2004, "Prostratin Antagonizes HIV Latency by Activating NF-κB." *J. Biol. Chem.* 279(40):42008-42017.

Witvrouw et al, 2003, "Potent and Selective Inhibition of HIV and SIV by Prostratin Interacting with Viral Entry," *Antivir Chem Chemother.* 14(6):321-328.

Zayed et al., "New Tigliane and Daphnane Derivatives from *Pimelea prostrata* and *Pimelea simplex*." 1977, *Experentia* 33(12):1554-5.

Zhao et al., 1988, "Diterpenes and Sterols from *Neoboutonia melleri*," *Phytochemistry* 48(7):1173-1177.

Kim, S. and Winkler, J.D., "Approaches to the synthesis of ingenol," *Chem. Soc. Rev.* 26:387-399 (1997).

Guillory, J.K., "Generation of Polymorphs, Hydrates, Solvates, and Amorphous Solids," In *Polymorphism in Pharmaceutical Solids*, H.G. Brittain ed., pp. 183-226, Informa Health Care (2007).

\* cited by examiner

ESTER PRODRUGS OF PROSTRATIN AND RELATED PHORBOL COMPOUNDS

1. CROSS REFERENCE TO RELATED APPLICATIONS

This application is a National Stage of International Application No. PCT/US2006/027303, filed Jul. 13, 2006, which claims benefit under 35 U.S.C. §119(e) of U.S. application Ser. No. 60/699,047, filed Jul. 13, 2005, the contents of which are incorporated herein by reference.

2. TECHNICAL FIELD

The present disclosure relates to analogs and derivatives of phorbol compounds, their synthesis, and methods of using the compounds.

3. BACKGROUND

While highly active antiretroviral therapy (HAART) is helping many people with HIV/AIDS live longer, healthier lives, these combination or "cocktail" treatments are not always effective and often cause serious adverse side effects. Even among those who do well on HAART, many patients experience treatment failure within a year or two, often because HIV has developed resistance to the drugs used to inhibit its growth. Drug resistant HIV tends to progressively develop resistance to other drugs in the same class, or even to the entire class of drugs. In addition, many people newly infected with HIV may carry viral strains already resistant to current treatments.

Confounding the resistance challenge is the latency of HIV infection. Despite the success of HAART, medical reports suggest that antiretroviral therapy alone is unable to eliminate the viral infection because the virus can persist in a latent form when infected $CD4^+$ lymphoblasts carrying an integrated copy of the HIV-1 genome revert back to a resting memory state. In this state, CD4 cells are minimally permissive for virus gene expression, and infected memory cells can survive for many years. Following reexposure to the relevant antigen or other activating stimuli, these cells can begin to produce virus again. Though HAART may be effective for an acute infection, it appears unable to eliminate this viral reservoir, which can serve as a permanent archive for wild-type virus and for drug-resistant variants that arise during treatment. Thus, once resistance to a particular drug arises, the patient may always carry that resistant viral strain (Siliciano et al., 2004, *J. Antimicrobial Chemo.* 54:6-9).

Commonly used anti-HIV therapies generally target two viral enzymes that HIV needs to reproduce: reverse transcriptase and protease. A third therapeutic approach is to target the binding of the virus to the cell, thereby affecting the viral entry phase of the HIV replication cycle. An example of the latter therapy is enfurvirtide (Fuzeon®), a linear 36 amino acid peptide that binds to the heptad repeat in the gp41 viral envelope glycoprotein on $CD4^+$ cells. However, because of the problems associated with drug resistance and virus latency, there is a need for new therapeutic approaches based on anti-viral agents that are structurally and/or mechanistically different from the currently approved compounds. One such approach is represented by the anti-viral properties of phorbol compounds prostratin (see, e.g., U.S. Pat. No. 5,599, 839) and ingenol (see, e.g., Fujiwara et al., 1996, *Antimicrob Agents Chemother.* 40(1):271-3).

Prostratin, 12-deoxyphorbol 13-acetate, was first isolated from *Pimelea prostrata*, a New Zealand plant toxic to livestock (Zayed S., 1977, *Experentia* 33(12):1554-5). Prostratin was subsequently isolated from *Homalanthus nutans*, a medicinal plant used by traditional Samoan healers, and shown to inhibit HIV-induced cell killing and viral replication in a variety of cell systems (Cox et al, 1993, *J. Ethnopharmacol.* 38(2-3):181-8; Cox, P.A., 1994, *Ciba Found. Symp.* 185:25-36). The potency and degree of cytoprotection is dependent on both viral strain and host cell type (Gustafson et al, 1992, *J. Med. Chem.* 35(11):1978-86).

Similarly, ingenol compounds were used in traditional medicine for the treatment of skin conditions (e.g., warts, corns, etc.), cancer, and asthma (Green et al., 1988, *Australian J Dermatol* 29:127-30 and Weedon et al., 1976, *Med J of Australia* 1:928). Ingenol-3,5,20-triacetate has also been show to have anti-viral properties (Fujiwara et al., supra).

Interestingly, studies suggest that prostratin displays a unique dual effect on HIV biology: inhibiting HIV replication while activating dormant or "latent" HIV that hides in human cells (Kulkosky et al., 2001, *Blood.* 98(10):3006-15). Prostratin efficiently reactivates HIV expression from latently infected cells generated in a SCID-hu mouse. Reactivation is associated with induction of viral transcription from the HIV long terminal repeat (LTR) and is thought to involve prostratin's property of activating specific protein kinase C (PKC) isozymes. Prostratin also appears to inhibit the entry step of the HIV replication cycle by interacting with a cellular target necessary for viral entry and/or by downregulating HIV co-receptors CCR5 and CXR5 (Witvrouw et al, 2003, *Antivir Chem. Chemother.* 14(6):321-8). Prostratin's unique mechanism of action is indicated by its effectiveness against different strains of HIV-1, such as HIV subtypes B and D, clinical HIV isolate (L1), HIV-2 (ROD and EHO), and SIV (MA C 251) and effectiveness against HIV strains resistant to polyanionic binding inhibitor dextran sulfate, the fusion inhibitor enfuvirtide, nucleoside reverse transcriptase inhibitors (NRTs), and protease inhibitor (PIs) (Witvrouw et al., supra). Likewise, ingenols with antiviral activity appear to affect the viral absorption process rather than the viral replication machinery (Fugiwara et al., supra). Studies further suggest that ingenol compounds may also cause reactivation of latent viruses, similar to the effects seen with prostratin (Fujiwara et al., 1998, *Arch Virol.* 143(10):2003-10)

Although prostratin and related phorbol compounds present an attractive therapeutic strategy for HIV in view of their reactivation and antiviral properties, as well as treatments for other diseases affected through phorbol mediated signal transduction pathways, the therapeutic effectiveness of these phorbol compounds is limited by their low solubility, low oral bioavailability, and low therapeutic index.

4. SUMMARY

The present disclosure provides analogs and derivatives of prostratin and related phorbol compounds, methods of making the compounds, and methods of using the compounds to treat various conditions and diseases. The phorbol compounds disclosed herein are prodrugs of phorbol esters that have various biological activities, including binding to phorbol receptors and modulation of associated signal transduction pathways, reactivation of latent viruses and inhibition of viral absorption, and tumor promoting properties as well as tumor promoter inhibiting activity. In relation to these biological effects, the prodrugs find uses in treating pain, cell proliferative disorders, inflammatory reactions, and viral infections.

In some aspects, the compounds disclosed herein are prodrug compounds according to structural formula (I):

R—X—O—C(O)—R'  (I)

including salts and hydrates thereof, wherein:
R is a residue of a phorbol ester;
X is an alkylene chain containing from 1 to 12 carbon atoms;

R' is a moiety that either bears a permanent charge or that is ionizable at a pH in the range of about 2 to about 8;

the illustrated —X—O—C(O)—R' group is linked to the 6-carbon of R; and the illustrated —X—O—C(O)—R' group hydrolyzes under biological conditions to yield a group of the formula —X—OH.

In some embodiments of the compound of structural formula (I), the X is methano (—CH$_2$—) and R' is a group that comprises a carboxyl group or a salt thereof.

In some embodiments, the R' is a group of the formula —(CH$_2$)$_m$—C(O)OM, where M is hydrogen or a counter ion and m is an integer ranging from 1 to 4.

In some embodiments, the R' can be selected from —(CH$_2$)$_n$—CH[(CH$_2$)$_n$—NH$_2$]—(CH$_2$)$_n$—C(O)OM and —(CH$_2$)$_n$—CH(NH$_2$)—(CH$_2$)$_n$—C(O)OM, where M is as defined as above and each n is, independently of the others, an integer ranging from 0 to 4.

In some embodiments, the R' of the phorbol compounds of structural formula (I) is a group of the formula —Y—Z, wherein:

Y is a branched or unbranched, saturated or unsaturated alkylene chain containing from 1 to 4 carbon atoms;

Z is selected from —C(O)OM, —NR$^b$R$^b$ and —NR$^c$R$^c$R$^c$;

M is hydrogen or a counter ion;

each R$^b$ is, independently of the other, selected from hydrogen, lower alkyl, lower hydroxyalkyl and lower alkoxyalkyl, heteroalkyl or, alternatively, two R$^b$ groups bonded to the same nitrogen atom may be taken together with the nitrogen atom to which they are bonded to form a 5- to 7-membered heteroatomic ring; and each R$^c$ is, independently of the others, selected from lower alkyl, lower hydroxyalkyl and lower alkoxyalkyl.

In some embodiments, R is selected from structures (R1) and (R2):

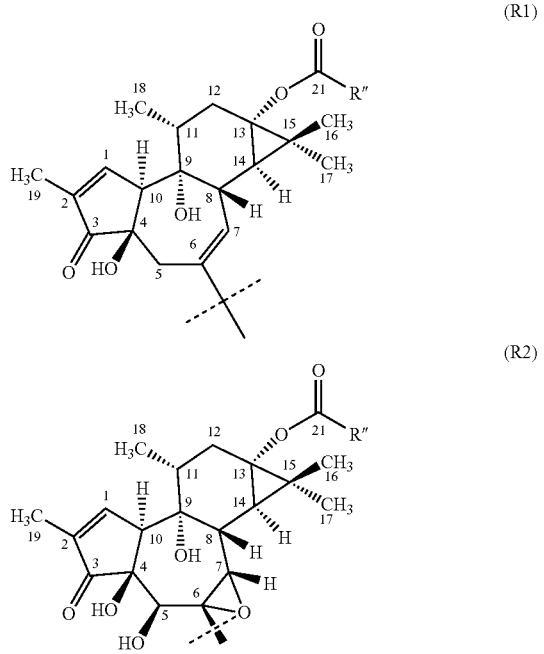

wherein:

R" is selected from (C$_1$-C$_{14}$) alkyl and benzyl.

In other aspects, provided herein are pharmaceutical compositions of the prodrug compounds, or pharmaceutically acceptable salts and hydrates thereof, and a pharmaceutically acceptable vehicle, such as an excipient, diluent or carrier. The choice of vehicle will depend upon, among other factors, the mode of administration.

In some aspects, the prodrug compounds can be used to modulate the activity of a phorbol receptor, or a signal transduction cascade dependent thereon. Generally, the method comprises administering to a cell the prodrug compound under conditions in which the progroup cleaves to generate an active phorbol compound.

In other aspects, the prodrug compounds can be used to treat various conditions or diseases, such as neoplasms, viral infections, inflammatory conditions, and pain. The methods comprise administering to a subject afflicted with the condition or disease an amount of the prodrug compound effective to treat the condition or disease. The compounds can also be used as prophylaxis in reducing the risk of the occurrence of the condition or disease.

Further provided herein are kits comprising the prodrug compounds. The compounds can be provided as pharmaceutical compositions in various dosage forms and dosage units for administration.

5. DETAILED DESCRIPTION 5.1 Definitions

As used throughout the instant application, the following terms shall have the following meanings:

"Alkyl" by itself or as part of another substituent refers to a saturated or unsaturated branched, straight-chain or cyclic monovalent hydrocarbon radical having the stated number of carbon atoms (i.e., C$_1$-C$_6$ means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree of level of saturation, e.g., groups having exclusively single carbon-carbon bonds, groups having one or more double carbon bonds, groups having mixtures of single, double, and triple carbon-carbon bonds. Where specific levels of saturation are intended, the nomenclature "alkanyl," "alkenyl" and/or "alkynyl" is used, as defined below. In some embodiments, the alkyl group comprises from 1 to 20 carbon atoms (C$_1$-C$_{20}$). In some embodiments, the alkyl group comprises 1 to 10 carbon atoms (C$_1$-C$_{10}$). In some embodiments, an alkyl group comprises from 1 to 6 carbon atoms (C$_1$-C$_6$). The expression "lower alkyl" refers to alkyl groups comprised of from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc; and the like. In some embodiments, the alkenyl group is $(C_2-C_6)$ alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc; and the like. In some embodiments, the alkynyl group is $(C_2-C_6)$ alkynyl.

"Alkyldiyl" by itself or as part of another substituent refers to a saturated or unsaturated, branched, straight-chain or cyclic divalent hydrocarbon group having the stated number of carbon atoms (e.g., $C_1-C_6$ means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is $(C_1-C_6)$ alkyldiyl. In some embodiments, the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkyleno group is $(C_1-C_6)$ alkyleno. In some embodiments, the alkyleno group is $(C_1-C_3)$ alkyleno. In some embodiments, the alkyleno groups are straight-chain saturated alkano groups, e.g., methano, ethano, propano, butano, and the like.

"Acyl" by itself or as part of another substituent refers to $-C(O)R^5$, where $R^5$ is hydrogen, or substituted or unsubstituted alkyl, cylcoalkyl, cycloheteroalkyl, aryl, arylalkyl, heteroalkyl, heteroaryl, or heteroarylalkyl as defined herein. Typical acyl groups include, but are not limited to, formyl, acetyl, cyclohexylcarbonyl, cyclohexylmethylcarbonyl, benzoyl, benzylcarbonyl, and the like.

"Acyloxy" by itself or as part of another substituent refers to $-OC(O)R^6$, where $R^6$ represents a hydrogen, or substituted or unsubstituted alkyl, heteroalkyl, cycloalkyl, heterocycloalkyl, aryl, arylalkyl, and heteroaryl groups as defined herein. Alkylacyloxy refers an acyloxy where $R^6$ is $(C_1-C_{12})$ alkyl, $(C_1-C_8)$ alkyl, or $(C_1-C_4)$ alkyl. Arylacyloxy refers to an acyloxy where $R^6$ is an aryl optionally substituted with selected substituents, including, but not limited to, hydroxyl, alkyl, halogen, $(C_1-C_4)$ alkyl, $(C_1-C_4)$ alkoxy, and carboxyl.

"Alkoxy" by itself or as part of another substituent refers to $-OR^7$, where $R^7$ represents an alkyl or cycloalkyl group as defined herein. Typical alkoxy groups include, but are not limited to, methoxy, ethoxy, propoxy, butoxy, cyclohexyloxy, and the like.

"Alkoxycarbonyl" by itself or as part of another substituent, refers to $-C(O)OR^8$ where $R^8$ represents an alkyl or cycloalkyl group as defined herein. Typical alkoxycarbonyl groups include, but are not limited to, methoxycarbonyl, ethoxycarbonyl, proproxycarbonyl, butoxycarbonyl, cyclohexyloxycarbonyl, and the like.

"Amino" by itself or as part of another substituent refers to the group $-NH_2$. Substituted amino refers to the group $-NHR^9$, $NR^9R^9$, and $NR^9R^9R^9$, where each $R^9$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylamino, triethylamino, methylsulfonylamino, furanyl-oxy-sulfamino, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, $-O-$, $-S-$, $-S-O-$, $-NR^{10}-$, $-PR^{10}-$, $-S(O)-$, $-S(O)_2-$, $-S(O)NR^{10}-$, $-S(O)_2NR^{10}-$, etc., including combinations thereof, where each $R^{10}$ is independently hydrogen, or substituted or unsubstituted alkyl, aryl, arylalkyl, cycloalkyl, cycloheteroalkyl heteroalkyl, heteroaryl, or heteroarylalkyl.

"Cycloalkyl" by itself or as part of another substituent refers to a saturated or unsaturated cyclic alkyl derived by removal of one hydrogen from the parent cyclic alkyl. Where a specific level of saturation is intended, the nomenclature "cycloalkanyl" or "cycloalkenyl" is used. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. In some embodiments, the cycloalkyl group is $(C_3-C_{10})$ cycloalkyl. In other embodiments, the cycloalkyl group is $(C_3-C_7)$ cycloalkyl.

"Cycloheteroalkyl" by itself or as part of another substituent refers to a saturated or unsaturated cyclic alkyl in which one or more carbon atoms (and any associated hydrogen atoms) are independently replaced with the same or different heteroatom. Typical heteroatoms to replace the carbon atom include but are not limited to N, P, O, S, etc. A heteroatom can occupy the position that is attached to the remainder of the molecule. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), pyrrolidinyl, etc.; and the like.

"Parent Aromatic Ring System" refers to an unsaturated cyclic or polycyclic ring system having a conjugated electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, etc., as well as the various hydro isomers thereof.

"Aryl" by itself or as part of another substituent refers to a monovalent aromatic hydrocarbon group having the stated number of carbon atoms (i.e., $C_5-C_{15}$ means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group comprises $(C_5-C_{15})$ aryl. In other embodiments, the aryl group comprises $(C_5-C_{10})$ aryl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is $(C_6-C_{21})$ arylalkyl, e.g., the alkanyl, alkenyl or alkynyl moiety of the arylalkyl group is $(C_1-C_6)$ and the aryl moiety is $(C_5-C_{15})$. In other embodiments the arylalkyl group is $(C_6-C_{13})$, e.g., the alkanyl, alkenyl or alkynyl moiety of the arylalkyl group is $(C_1-C_3)$ and the aryl moiety is $(C_5-C_{10})$.

"Aryloxy" by itself or as part of another substituent, refers to a radical of the formula —O-aryl, where aryl is as defined herein.

"Arylalkyloxy" by itself or as part of another substituent, refers to a radical of the formula —O-arylalkyl, where arylalkyl is as defined herein.

"Aryloxycarbonyl" by itself or as part of another substituent, refers to a radical of the formula —C(O)—O-aryl, where aryl is as defined herein.

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), $S(O)_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, -carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxaxine, benzoxazole, benzoxazoline, carbazole, -carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In some embodiments, the heteroaryl group is a 5-20 membered heteroaryl. In other embodiments, the heteroaryl group is a 5-10 membered heteroaryl.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-20 membered heteroarylalkyl, e.g., the alkanyl, alkenyl or alkynyl moiety of the heteroarylalkyl is ($C_1$-$C_{10}$) alkyl and the heteroaryl moiety is a 5-12-membered heteroaryl. In some embodiments, the heteroarylalkyl is a 6-13 member heteroarylalkyl, e.g., the alkanyl, alkenyl or alkynyl moiety of the heteroarylalkyl is ($C_1$-$C_3$) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "($C_1$-$C_2$) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —$OR^7$, as defined above; "alkylamine" refers to a group of the formula —$NHR^{11}$; and "dialkylamine" refers to a group of the formula —$NR^{11}R^{11}$, where each $R^{11}$ is independently an alkyl. As another example, "haloalkoxy" or "haloalkyloxy" refers to a group of the formula —$OR^{12}$, where $R^{12}$ is a haloalkyl.

"Substituted" when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^{13}$, halo, —$O^-$, =$O$, —$OR^{14}$, —$SR^{14}$, —$S^-$, =$S$, —$NR^{15}R^{15}$, =$NR^{14}$, =$N$—$OR^{14}$, trihalomethyl, —$CF_3$, —CN, —OCN, —SCN, —NO, —$NO_2$, =$N_2$, —$N_3$, —$S(O)_2R^{14}$, —$S(O)_2O^-$, —$S(O)_2OR^{14}$, —$OS(O)_2R^{14}$, —$OS(O)_2O^-$, —$OS(O)_2OR^{14}$, —$P(O)(O^-)_2$, —$P(O)(OR^{14})(O^-)$, —$P(O)(OR^{14})(OR^{14})$, —$C(O)R^{14}$, —$C(S)R^{14}$, —$C(NR^{14})R^{14}$, —$C(O)O^-$, —$C(O)OR^{14}$, —$C(S)OR^{14}$, —$C(O)NR^{15}R^{15}$, —$C(NR^{14})NR^{15}R^{15}$, —$OC(O)R^{14}$, —$OC(S)R^{14}$, —$OC(O)O^-$, —$OC(O)OR^{14}$, —$OC(S)OR^{14}$, —$NR^{14}C(O)R^{14}$, —$NR^{14}C(S)R^{14}$, —$NR^{14}C(O)O^-$, —$NR^{14}C(O)OR^{14}$, —$NR^{14}C(S)OR^{14}$, —$NR^{14}C(O)NR^{15}R^{15}$, —$NR^{14}C(NR^{14})R^{14}$ and —$NR^{14}C(NR^{14})NR^{15}R^{15}$, where $R^{13}$ is selected from the group consisting of alkyl, cycloalkyl, heteroalkyl, cycloheteroalkyl, aryl, arylalkyl, heteroaryl and heteroarylalkyl; each $R^{14}$ is independently hydrogen or $R^{13}$; and each $R^{15}$ is independently $R^{14}$ or alternatively, the two $R^{15}$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^{15}R^{15}$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^{13}$, halo, —$O^-$, —$OR^{14}$, —$SR^{14}$, —$S^-$, —$NR^{15}R^{15}$, trihalomethyl, —$CF_3$, —CN, —OCN, —SCN, —NO, —$NO_2$, —$N_3$, —$S(O)_2R^{14}$, —$S(O)_2O^-$, —$S(O)_2OR^{14}$, —$OS(O)_2R^{14}$, —$OS(O)_2O^-$, —$OS(O)_2OR^{14}$, —$P(O)(O^-)_2$, —$P(O)(OR^{14})(O^-)$, —$P(O)(OR^{14})(OR^{14})$, —$C(O)R^{14}$, —$C(S)R^{14}$, —$C(NR^{14})R^{14}$, —$C(O)O$—, —$C(O)OR^{14}$, —$C(S)OR^{14}$, —$C(O)NR^{15}R^{15}$, —$C(NR^{14})NR^{15}R^{15}$, —$OC(O)R^{14}$, —$OC(S)R^{14}$, —$OC(O)O$—, —$OC(O)R^{14}$, —$OC(S)OR^{14}$, —$NR^{14}C(O)R^{14}$, —$NR^{14}C(S)R^{14}$, —$NR^{14}C(O)O$—, —$NR^{14}C(O)OR^{14}$, —$NR^{14}C(S)OR^{14}$, —$NR^{14}C(O)NR^{15}R^{15}$, —$R^{14}C(NR^{14})R^{14}$ and —$NR^{14}C(NR^{14})NR^{15}R^{15}$, where $R^{13}$, $R^{14}$ and $R^{15}$ are as previously defined.

Substituent groups useful for substituting nitrogen atoms in heteroalkyl and cycloheteroalkyl groups include, but are not limited to, —$R^{13}$, —$O$—, —$OR^{14}$, —$SR^{14}$, —$S^-$, —$NR^{15}R^{15}$, trihalomethyl, —$CF_3$, —CN, —NO, —$NO_2$, —$S(O)_2R^{14}$, —$S(O)_2O^-$, —$S(O)_2OR^{14}$, —$OS(O)_2R^{14}$, —$OS(O)_2O^-$, —$OS(O)_2OR^{14}$, —$P(O)(O^-)_2$, —$P(O)(OR^{14})$ ($O^-$), —$P(O)(OR^{14})(OR^{14})$, —$C(O)R^{14}$, —$C(S)R^{14}$, —$C(NR^{14})R^{14}$, —$C(O)OR^{14}$, —$C(S)OR^{14}$, —$C(O)NR^{15}R^{15}$, —$C(NR^{15})NR^{15}R^{15}$, —$OC(O)R^{14}$, —$OC(S)R^{14}$, —$OC(O)OR^{14}$, —$OC(S)OR^{14}$, —$NR^{14}C(O)R^{14}$, —$NR^{14}C(S)R^{14}$, —$NR^{14}C(O)OR^{14}$, —$NR^{14}C(S)OR^{14}$, —$NR^{14}C(O)NR^{15}R^{15}$, —$NR^{14}C(NR^{14})R^{14}$ and —$NR^{14}C(NR^{14})NR^{15}R^{15}$, where $R^{13}$, $R^{14}$ and $R^{15}$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Protecting group" refers to a group of atoms that, when attached to a reactive functional group in a molecule, masks, reduces or prevents the reactivity of the functional group. Typically, a protecting group may be selectively removed as desired during the course of a synthesis. Examples of protecting groups can be found in Greene et al., *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active phorbol compound (drug) that requires a transformation under the conditions of use, such as within the body, to release the active phorbol compound. Prodrugs are frequently, but not necessarily, pharmacologically inactive until converted into the active drug. Prodrugs are typically obtained by masking a functional group in the phorbol compound believed to be in part required for activity with a progroup (defined below) to form a promoiety which undergoes a transformation, such as cleavage, under the specified conditions of use to release the functional group, and hence the active phorbol compound. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active phorbol compound to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use.

"Phorbol" refers to diterpenoid compounds based on the polycyclic structures of formulas (II) and (III):

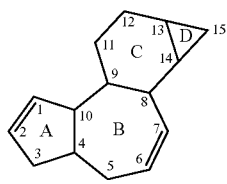

(II)

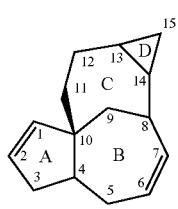

(III)

wherein one or more substituents can be present on each of rings A, B, C and D. Substituents can be any substituents typically present on phorbol compounds, including but not limited to, hydroxyl, alkyl, heteroalkyl, alkoxy, hydroxyalkyl, arylalkoxy, alkoxycarbonyl, aldehyde, acyloxy, and combinations of these groups. The numbering of atoms in the core polycyclic structure of the phorbol compounds will follow those indicated above. Exemplary phorbols include compounds based on the following structures:

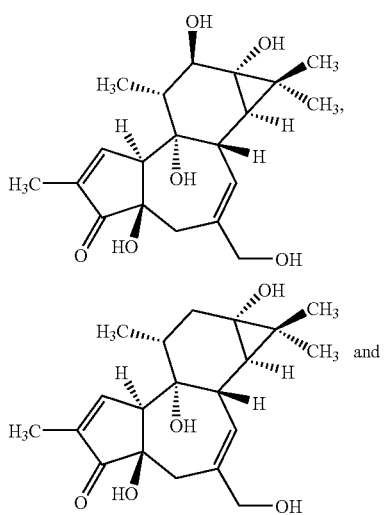

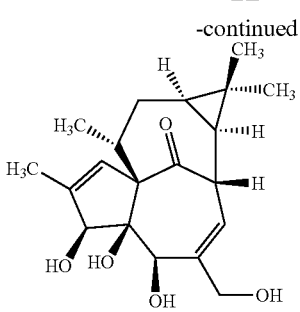

"Phorbol ester" refers to phorbol compounds substituted with any acyloxy group, with exemplary phorbol esters having esters at the 12 and/or 13 positions of the compounds based on structural formula (II) and at the 3, 4 and 5 positions of the compounds based on structural formula (III).

"Phorbol receptor" refers to a biological moiety that binds phorbol compounds. The biological moiety may bind to the phorbol compound in vitro, where the biological moiety is in a crude, semi-purified, or purified form. In various other embodiments, the biological moiety is present in vivo. The binding can occur independently or in cooperation with other components that associate with the biological moiety. Generally, the binding of the phorbol compound will have sufficient specificity to elicit a biological activity and/or interfere with the binding of other agents that interact with the biological moiety in a similar or identical region bound by the phorbol compounds.

"Tumor promoter" refers to an agent, such as a compound or composition, that in classical studies of carcinogenesis is able to increase the sensitivity of tumor formation by a previously applied primary carcinogen, but which generally does not efficiently induce tumors when used alone. However, tumor promoters may display carcinogenic properties when tested under more stringent or sensitive conditions. Exemplary tumor promoters are the compounds found in croton oil, active ingredients of which are believed to be phorbol esters and variations thereof.

"Non-tumor promoting phorbol" refers to a phorbol compound that displays at least one of the biological activities of phorbol compounds, such as binding to phorbol receptors, but which do not show tumor promoting properties. Exemplary "non-tumor promoting" phorbol compounds include, but are not limited to, 12-deoxyphorbol 13-acetate (i.e., prostrating, 12-dexoxyphorbol 13-propanoate, and 12-dexoxyphorbol 13-phenylacetate.

"Biological conditions" refer to any condition that is a physiological condition present in vivo, or an in vitro condition that mimics the physiological condition. For the purposes herein, the phrase "hydrolysable under biological conditions" refers to a physiological condition that results in removal of the progroup moiety to produce the biologically active compound. Thus, where removal of the progroup occurs by action of an enzyme, the biological condition comprises such enzyme to cause removal of the progroup. Where removal of the progroup occurs spontaneously, such as by hydrolysis, the biological condition comprises the physiologic condition that results in spontaneous loss of the progroup.

5.2 Analogs and Derivatives of Phorbol Compounds

The phorbol compounds of the present disclosure are prodrugs that are more soluble in various mediums for administration than the active form of the phorbol compounds. In the embodiments disclosed herein, the phorbol compounds are generally based on a diterpenoid compound comprising "core" polycyclic structures according to structural formulas (II) and (III):.

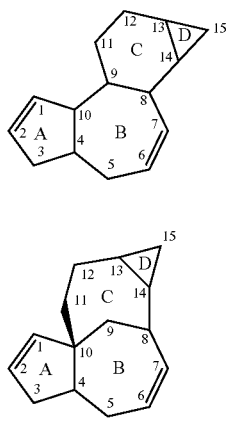

(II)

(III)

As noted above, one or more substituents can be present on each of rings A, B, C, and D. Typical substituents include, but are not limited to, hydroxyl, hydroxyalky, alkyl, heteroalkyl, alkoxy, arylalkoxy, alkoxycarbonyl, aldehyde, acyloxy and combinations of these groups (see, e.g., *Naturally Occurring Phorbol Esters*, F. J. Evans ed., 1986, CRC Press, Boca Raton, Fla.). In some embodiments, the phorbol compounds are based on the structural formulas (IIa) and (IIIa):

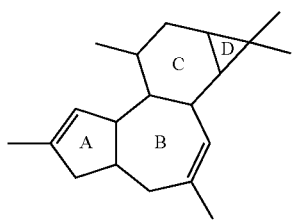

(IIa)

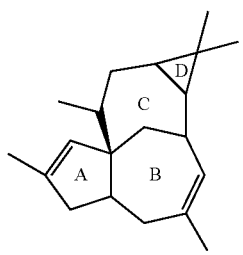

(IIIa)

Various derivatives and analogs of the above compounds occur naturally with various substituents present on rings A, B, C, and D, and have also been made by synthetic methods. The compounds can also have additional modifications of the substituents shown in the parent structure. Thus in some embodiments, the phorbol compounds herein relate to compounds of the structural formulas (IIb), (IIc), and (IIIb):

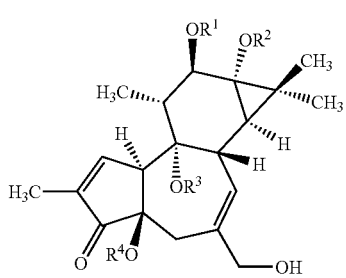

(IIb)

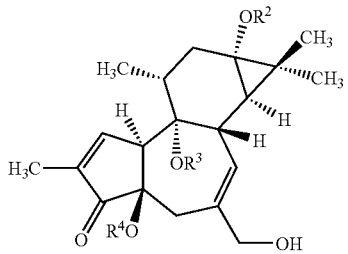

(IIc)

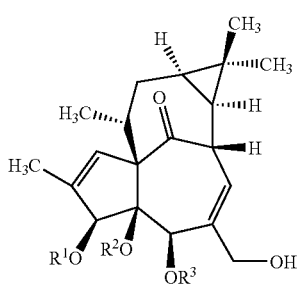

(IIIb)

wherein $R^1$, $R^2$, $R^3$, and $R^4$ is, independently of one another, selected from a hydrogen or an acyl —C(O)R″, where R″ is hydrogen, or substituted or unsubstituted alkyl, aryl, arylalkyl, heteroalkyl, heteroaryl, or heteroarylalkyl as defined herein. In some embodiments, the R″ is selected from methyl, unsaturated lower alkyl, lower n-alkyl, benzyl, 4-hydroxybenzyl, 4-methoxybenzyl, and 4-acetyloxybenzyl. In some embodiments, an oxygen atom is added to the double bond between carbon atoms 6 and 7 such that the phorbol compound has an epoxide in ring B. In various embodiments, the phorbol compounds in the present disclosure are active phorbol compounds. As used herein, active phorbol compound refers to a phorbol displaying at least one of the biological activities associated with phorbol compounds, as further described herein (e.g., binding to a phorbol receptor, tumor promotion, anti-viral activity, etc). Without being bound by theory, active phorbol compounds with an —OH substituent on position 4 carbon have been shown to be in the β conformation while inactive compounds are in the α conformation (see, e.g., Silinsky et al., 2003, *Br J Pharmacol.* 138(7):1191-201).

In some embodiments, exemplary compounds of the present disclosure are analogs and derivatives of the following phorbol compound:

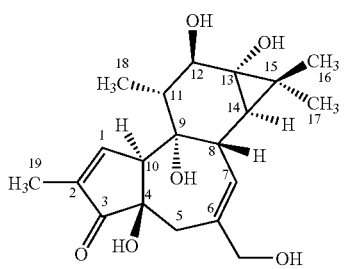

The phorbol compounds disclosed herein also include analogs and derivatives of 12-deoxyphorbol based on the following structure:

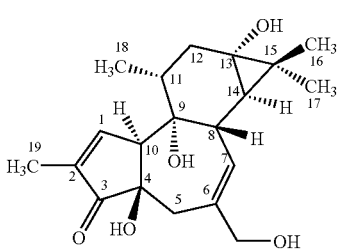

In other embodiments, the phorbol compounds disclosed herein are analogs and derivatives of ingenol compound based on the following structure:

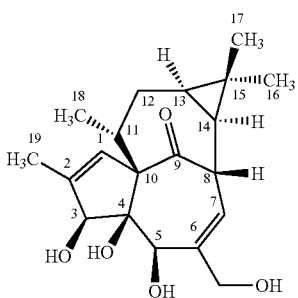

As note above, additional substituents can be present on rings A, B, C, and D, along with modifications to the hydroxyl and/or methyl groups present throughout the phorbol structure. The numbering of the substituents follows the convention given above. In some embodiments, the compounds herein comprise esters of the phorbol compounds, where the ester is present on any of the rings or the substituents of the parent phorbol structures. Many phorbol compounds based on structural formula (II) have ester groups on the 12-carbon and/or 13-carbon position of the compounds above. Exemplary phorbol esters include, but are not limited to, 12-deoxyphorbol 13-acetate, 12-deoxyphorbol 13-phenylacetate; 12-deoxyphorbol 13-propanoate; 12-deoxyphorbol 13-isobutyrate; 12-deoxyphorbol 13-myristate; 12-deoxyphorbol 13-tetradecanoate; 12-deoxyphorbol 13-angelate; phorbol 13-acetate; phorbol 13-myristate; phorbol-12,13-diacetate; phorbol-12, 13-dibutyrate; phorbol-12,13-didecanoate; phorbol-12-myristate 13-acetate; phorbol-12, 13-dibenzoate; and phorbol-12-acetate 13-tigliate. Phorbol compounds based on structural formula (III) has esters and the 3, 4 and 5 positions, and in some embodiments, the 20 carbon position. Exemplary phorbol esters of the ingenol compounds for the prodrugs herein include, but are not limited to, ingenol 3 acetate, ingenol-3-propionate, ingenol 3-palmitate, ingenol-3-angelate, and ingenol 3-benzoate. Other phorbol esters that are suitable for the purposes herein will be apparent to the skilled artisan.

In some aspects, the phorbol compounds are prodrug compounds according to structural formula (I):

R—X—O—C(O)—R'     (I)

including salts and hydrates thereof, wherein:
R is a residue of a phorbol ester;
X is an alkylene chain containing from 1 to 12 carbon atoms;
R' is a moiety that either bears a permanent charge or that is ionizable at a pH in the range of about to about 2.0-8.0, a pH in the range of about 4.0-7.4, or a pH in the range of about 6.8-7.4;
the illustrated —X—O—C(O)—R' group is linked to the 6-carbon of R; and
the illustrated —X—O—C(O)—R' group hydrolyzes under biological conditions to yield a group of the formula —X—OH.

In some embodiments, the X of structural formula I is a methano (—CH$_2$—). The R' is a group that comprises a carboxyl group, such as a carboxyl-substituted lower alkyl, or a salt thereof.

In some embodiments, the R' is a group of the formula —(CH$_2$)$_m$—C(O)OM, where M is hydrogen or a counter ion and m is an integer ranging from 1 to 4. The counter ion can be any ion that can form an ionic bond with the ionized oxygen atom of the carboxyl group. Exemplary counter ions include, but are not limited to, Na$^+$ or K$^+$ or an organic base such as ethanolamine, diethanolamine, triethanolamine, morpholines, as further described below.

In some embodiments, the R' of the compounds further comprises an amino group. In some embodiments, the amino group can be an amino acid. In some embodiments, R' can be selected from —(CH$_2$)$_n$—CH[(CH$_2$)$_n$—NH$_2$]—(CH$_2$)$_n$—C(O)OM and —(CH$_2$)$_n$—CH(NH$_2$)—(CH$_2$)$_n$—C(O)OM, where M is as defined as above and each n is, independently of the others, an integer ranging from 0 to 4.

In other embodiments, the R' of structure (I) is a group of the formula —Y—Z, wherein:
Y is a branched or unbranched, saturated or unsaturated alkylene chain containing from 1 to 4 carbon atoms;
Z is selected from —C(O)OM, —NR$^b$R$^b$ and —NR$^c$R$^c$R$^c$;
M is hydrogen or a counter ion;
each R$^b$ is, independently of the other, selected from hydrogen, lower alkyl, lower hydroxyalkyl and lower alkoxyalkyl, heteroalkyl or, alternatively, two R$^b$ groups bonded to the same nitrogen atom can be taken together with the nitrogen atom to which they are bonded to form a 5- to 7-membered heteroatomic ring (e.g., cycloheteroalkyl),
each R$^c$ is, independently of the others, selected from lower alkyl, lower hydroxyalkyl and lower alkoxyalkyl.

In some embodiments of the phorbol compounds above,
any of the alkyl group or moiety is a branched or unbranched alkanyl;
Y is an alkano;
each R$^b$ is, independently of the other, selected from hydrogen and lower alkanyl;
each R$^c$ is, independently of the others, selected from lower alkanyl; and
NR$^b$R$^b$ is selected from morpholinyl, N-morpholinyl, piperazinyl, 1-piperazinyl, 1-methyl-piperazinyl and 1-methyl-4-piperazinyl. The Y can be selected from methano, ethano, propano and butano.

In some embodiments, independently the Z is —C(O)OM or selected from dimethyl amino, diethylamino, and N-morpholinyl.

In various embodiments described above, the core structure R can be selected from (R1) and (R2):

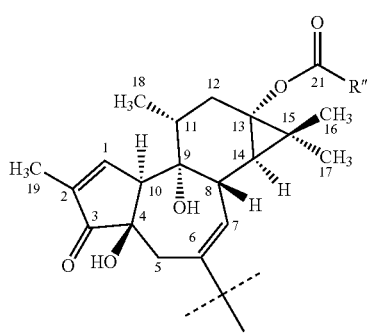

(R1)

-continued (R2)
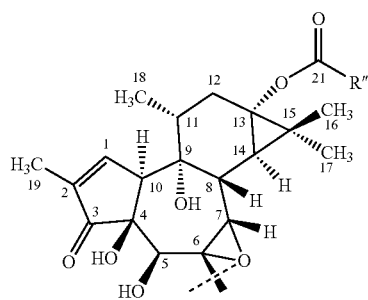

wherein:

R″ is selected from ($C_1$-$C_{14}$) alkyl and benzyl.

In some embodiments of compounds (R1) and (R2), the R″ is selected from methyl, unsaturated lower alkyl, lower n-alkyl, benzyl, 4-hydroxybenzyl, 4-methoxybenzyl, and 4-acetyloxybenzyl.

In some embodiments, the core structure R can be selected from (R3):

(R3)
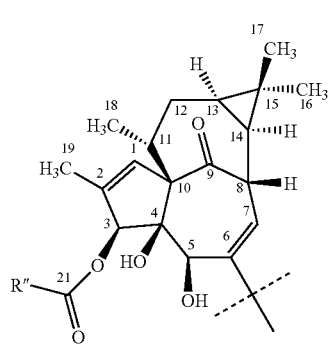

wherein:

R is selected from an alkyl, unsaturated lower alkyl, and benzyl.

In some embodiments of compounds (R3), the R″ is selected from methyl, branched alkenyl, lower n-alkyl, benzyl, 4-hydroxybenzyl, 4-methoxybenzyl, and 4-acetyloxybenzyl.

In further embodiments, the compounds have the structures (Ia) or (Ib):

(Ia)
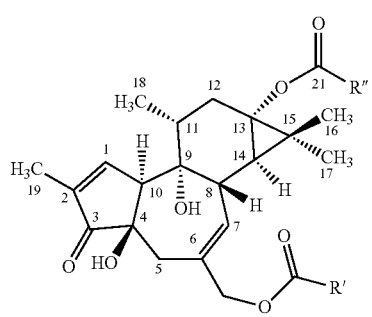

-continued (Ib)
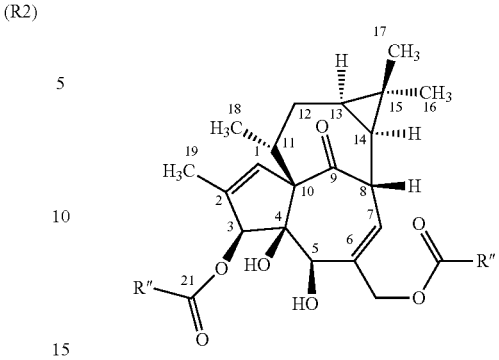

including the salts and hydrates thereof, wherein:

R″ is selected from lower substituted or unsubstituted alkyl, substituted or unsubstituted alkenyl, and benzyl.

In some embodiments of the compounds of structure (Ia) and (Ib), R' can be a group that comprises a carboxyl group, such as a carboxyl-substituted lower alkyl, or a salt thereof. The carboxyl group can be of the formula —$(CH_2)_m$—C(O)OM, where M is hydrogen or a counter ion and m is an integer ranging from 1 to 4.

In other embodiments of compound (Ia) and (Ib), the R' can comprise an amino group, such as an amino acid. Thus, the R can be selected from —$(CH_2)_n$—CH[$(CH_2)_n$—$NH_2$]—$(CH_2)_n$—C(O)OM and —$(CH_2)_n$—CH($NH_2$)—$(CH_2)_n$—C(O)OM, where M is as defined as above and each n is, independently of the others, an integer ranging from 0 to 4.

In some embodiments of compounds (Ia) and (Ib), the R' is a group of the formula —Y—Z, wherein:

Y is a branched or unbranched, saturated or unsaturated alkylene chain containing from 1 to 4 carbon atoms;

Z is selected from —C(O)OM, —$NR^bR^b$ and —$NR^cR^cR^c$;

M is as defined as above;

each $R^b$ is, independently of the other, selected from hydrogen, lower alkyl, lower hydroxyalkyl, lower alkoxyalkyl, and heteroalkyl or, alternatively, two $R^b$ groups bonded to the same nitrogen atom can be taken together with the nitrogen atom to which they are bonded to form a 5- to 7-membered heteroatomic ring; and each $R^c$ is, independently of the others, selected from lower alkyl, lower hydroxyalkyl and lower alkoxyalkyl.

As described previously, in the embodiments described above, the compound can have the features selected from:

any alkyl group or moiety is a branched or unbranched alkanyl;

Y is an alkano;

each $R^b$ is, independently of the other, selected from hydrogen and lower alkanyl;

each $R^c$ is, independently of the others, selected from lower alkanyl; and $NR^bR^b$ is selected from morpholinyl, N-morpholinyl, piperazinyl, 1-piperazinyl, 1-methyl-piperazinyl and 1-methyl-4-piperazinyl.

In some embodiments, Y is selected from methano, ethano, propano and butano.

Thus, in some embodiments, Z is selected from —C(O)OM, dimethylamino, diethylamino, trimethylamino, triethylamino, and N-morpholinyl.

In some embodiments of the structures R1, R2, R3, (Ia) and (Ib), R″ can be selected from methyl, ethyl, propyl, butyl, pentyl, and benzyl.

In some embodiments where —$NR^bR^b$ is in protonated form or —$NR^cR^cR^c$, the compound can further comprise a anionic counterion. Exemplary anionic counterions include, but is not limited to, Cl⁻, Br⁻, carboxylate ion, sulfonate ion, sulfate ion, acetate, oxalate, maleate, fumarate, methanesulfonate, or toluenesulfonate. Other suitable counterions will be apparent to the skilled artisan.

In the present disclosure, the compounds can be identified by either their chemical structure or their chemical name. When the chemical structure and the chemical name conflict, the chemical structure is determinative of the identity of the specific compound. Furthermore, the compounds described herein, as well as the various compound species specifically described and/or, illustrated herein, may exhibit the phenomena of tautomerism, conformational isomerism, geometric isomerism and/or optical isomerism. For example, the compounds and prodrugs can include one or more chiral centers and/or double bonds and as a consequence can exist as stereoisomers, such as double-bond isomers (i.e., geometric isomers), enantiomers and diasteromers and mixtures thereof, such as racemic mixtures. As another example, the compounds and prodrugs can exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the compound encompasses any tautomeric, conformational isomeric, optical isomeric and/or geometric isomeric forms of the compounds or prodrugs having one or more of the utilities described herein, as well as mixtures of these various different isomeric forms.

In various embodiments, depending upon the nature of the various substituents, the phorbol compounds of the present disclosure can be in the form of salts. Such salts include salts suitable for pharmaceutical uses ("pharmaceutically-acceptable salts"), salts suitable for veterinary uses, etc. Such salts can be derived from acids or bases, as is well-known in the art. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Pharmaceutically acceptable salts also include salts formed when an acidic proton present in the parent compound is either replaced by a metal ion (e.g., an alkali metal ion, an alkaline earth metal ion or an aluminum ion), or coordinates with an organic base (e.g., ethanolamine, diethanolamine, triethanolamine, N-methylglucamine, morpholine, piperidine, dimethylamine, diethylamine, etc., and the like).

5.3 Synthesis of Analogs and Derivatives

The compounds disclosed herein can be synthesized by a variety of different synthetic routes using commercially available starting materials and/or starting materials prepared by conventional synthetic methods.

In some embodiments, phorbol and related compounds can be isolated from various natural sources. Phorbol and Ingenol esters are present in various plants of the genus *Euphoriaceae*, including the Spurge and Poinsettia families (see, e.g., *Naturally Occurring Phorbol Esters*, F. J. Evans ed., 1986, CRC Press, Boca Raton, Fla.). Exemplary *Euphorbia* plants from which phorbol compounds have been isolated include, among others, *Euphorbia Fischeriana* (Liu et al., 1996, *Chinese Chemical Letters* 7(10):917-918), *Homalanthus nutans*, and *Homolanthus acuminatus*; *Neoboutonia melleri* (Zhao et al., 1988, *Phytochemistry* 48(7):1173-1177); *Excoecarcia agallocha* (Erickson et al., 1995, *J. Natural Products* 58(5): 769-72); and *Croton californicus* (Chavez et al., 1982, *J. Natural Products* 45(6):745-8). Phorbol epoxides of the structure R2 can also be obtained from natural sources. For example, Zayed et al., *Experientia* (1977), 33(12), 1554-5 describes the isolation of R2 from the *Pimelea prostrata* and *Pimelea simplex* plants. Various phorbol compounds, including 12-deoxyphorbol 13-acetate, are also available commercially (e.g., LC Laboratories, Woburn, Mass., USA; and Alexis, Switzerland) and can be used for the synthesis of the compounds disclosed herein. Exemplary plants from which ingenol esters can be obtained include, but are not limited to, *Euphorbia antiquorum*, *Euphorbia peplus*, *Euphorbia ingens* and *Euphorbia peplus* (see, e.g., Rizk et al., 1985, *Phytochemistry* 24:1605-6).

Methods for isolating phorbol compounds from natural sources will be apparent to the skilled artisan. For instance, an exemplary method for isolating 12-dexoxyphorbol 13-acetate (i.e., prostratin) is described in U.S. Pat. No. 5,599,839, incorporated herein by reference. Generally, plant extracts can be subjected to an alcohol and alcohol/organic solvent extraction and then processed by various partition methods (e.g., solvent partition). Additional purification can be obtained with various other techniques, including, among others, crystallization and chromatographic separation, such as gel exclusion, ion exchange, and HPLC chromatography.

Synthetic methods for producing phorbol parent compounds and related derivatives are also described in the art. Complete synthesis of phorbol can use Diels-Alder cycloaddition combined with aldol condensation (Wender et al., 1987, *J. Am. Chem. Soc.* 109:4390). Phorbol synthesis using oxidopyrilium [5+2] cycloaddition and zirconium mediated enyne-cyclization has also been described (Wender et al., 1989, *J. Am. Chem. Soc.* 111:8954; Wender et al., 1990, *J. Am. Chem. Soc.* 112:4959; Wender et al., 1997, *J. Am. Chem. Soc.* 119:12976). Assymetric synthesis of phorbol is given in Wender et al., 1997, *J. Am. Chem. Soc.* 119:7897. Another synthetic route using an intramolecular nitrile oxide [3+2] cycloaddition combined with an aldol condensation is described in Sugita et al., 1995, *Tetrahedron Lett.* 36:1067. Other references describing synthetic routes for phorbol compounds include Paquette et al., 1984, *J. Am. Chem. Soc.* 106:1446-1454; Rigby et al. *J. Org. Chem.* 55:2959-2962; Carroll et al., 2000, *Org. Lett.* 2(18):2873-2876; and Cha et al., 2001, *J Am Chem Soc* 123, 5590. Methods for synthesizing various derivatives of phorbol compounds are disclosed in, among others, U.S. Pat. Nos. 6,080,784, 5,962,498, 5,955, 501, 5,643,948, 5,145,842, WO 96/40614. Complete synthesis of ingenols are described in Nickel et al., 2004, *J Am Chem. Soc.* 126:16300 and Winkler et al., 2002, *J Am Chem. Soc.* 124 (33), 9726-9728. All publications incorporated herein by reference.

A variety of exemplary synthetic routes that can be used to synthesize the prodrug forms of the phorbol compounds are illustrated in Scheme (I).

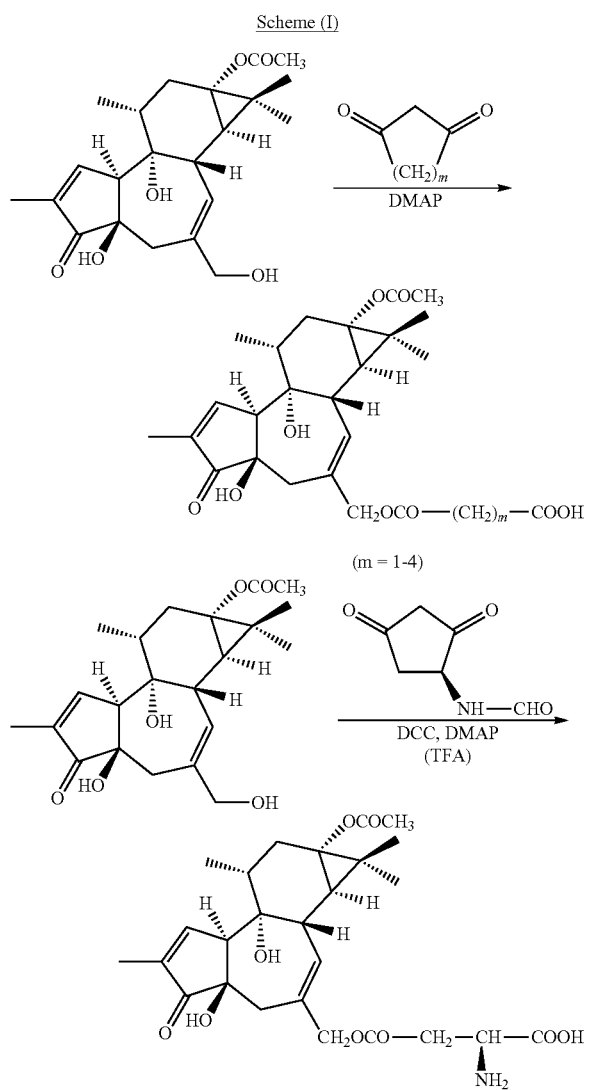

The synthetic methods of Scheme (I) generate the prodrug forms of 12-deoxyphorbol 13-acetate, either as the carboxylic acid or the amino acid. Generally, a dicarboxylic acid HOOC(CH$_2$)$_m$COOH is reacted in the presence of a coupling agent, such as an acylation catalyst 4-dimethylaminopyridine (DMAP) (see, e.g., U.S. Pat. No. 5,663,335, incorporated herein by reference). The coupling agent activates the dicarboxylic acid to promote reaction with the hydroxyl group. Use of a cyclic anhydride, substituted or unsubstituted, such as butanedioic anhydride (i.e., succinic anhydride) for the carboxylation also allows facile synthesis of the carboxylated phorbol. Where cyclic anhydrides are used, the coupling agent typically activates one of the two carbonyl carbons, promoting its attack by the hydroxyl group of the phorbol compound. Non-limiting examples of various cyclic anhydrides include, among others, substituted or unsubstituted 2-butendioic anhydride, pentanedioic anhydride, and hexanedioic anhydride.

Analogously, amino substituted R' of structural formula (I) can be synthesized using substituted dicarboxylic acids HOOC—(CH$_2$)$_n$—CH[(CH$_2$)$_n$—NH$_2$]—(CH$_2$)$_n$—COOH or HOOC—(CH$_2$)$_n$—CH(NH$_2$)—(CH$_2$)$_n$—COOH for generating the compounds in which the R' is —(CH$_2$)$_n$—CH[(CH$_2$)$_n$—NH$_2$]—(CH$_2$)$_n$—COOH or —(CH$_2$)$_n$—CH(NH$_2$)—(CH$_2$)$_n$—COOH. Use of substituted cyclic anhydride, as shown in Scheme (1), provides another method of synthesizing the amino substituted derivatives of the disclosed phorbol compounds.

Various amino ester derivatives can be prepared by reacting the phorbol starting compound with an amine substituted carboxylic acid in presence of a coupling reagent (e.g., DCC) and an acylating catalyst (e.g., DMAP) to synthesize the compound of structural formula (I) in which the R' is —Y—Z, wherein the Y is a branched or unbranched, saturated or unsaturated alkylene chain, and Z is the substituted amine. Use of a disubstituted amine yields the tertiary amine —NR$^b$R$^b$ while a trisubstituted amine yields the permanently charged quarternary amine —NR$^c$CR$^c$R$^c$. Non-limiting examples of amine substituted carboxylic acids useful in synthesis of the aminoester derivatives include, among others, N'N'-dimethylglycine, N'N'-dimethylproprionate, N'N'-dimethylbutanoate, N'N'N'-trimethylglycine, N'N'N'-trimethylpropionate, and N'N'N'-trimethylbutanoate. Other amine substituted carboxylic acids will be apparent to the skilled artisan.

For the disclosed phorbol compounds of structure (I) in which R' is —Y—Z, where Z is NR$^b$R$^b$ and the two R$^b$ groups are bonded to the same nitrogen to form a 5-7 heterocyclic ring, suitable carboxylic acids of morpholine, piperizine, pyrrolidine, and piperidine can be used. Non-limiting examples of heterocyclic carboxylic acids include, among others, 4-pyrrolidinobutyric acid and 5-morpholinopentanoic acid. Other heterocylic carboxylic acids will be apparent to the skilled artisan.

Where reactive groups on the phorbol compound require protection, they can be protected with a suitable protecting group. Oxygen atoms of hydroxyl groups can be protected in the form of acyl, benzyl, trialkylsilane, benzyloxycarbonyl, 4'-methoxyphenyldiphenylmethyl and trimethylsilylyethoxycarbonyl groups (Greene et al., *Protective Groups in Organic Chemistry*, 3$^{rd}$ Ed., 1999, John Wiley & Sons, NY). These groups have varying stabilities to or removed under acidic, basic or reducing conditions or with fluoride ion reagents, depending on the type of protecting group. Carbonyl functions can be protected by conversion to acetals or ketals, or by reduction to the alcohol level followed by protection with standard protecting groups for the hydroxy group. The hydroxy group at 2-position carbon of the phorbol compounds can be capped by reaction with substituted or unsubstituted alkyl, aryl, or aralkyl isocyanate in the presence of a catalyst such as dibutyltin dilaurate. For example, the oxygen atoms at position 3, 4, 12, and 13 of the parent phorbol compound or positions 3, 4, and 13 of the parent 12-deoxyphorbol compound can be blocked with a suitable protecting group chosen from the oxygen atom protecting groups described above. Other methods of protecting functional groups for synthesizing the compounds herein will be apparent to the skilled artisan.

5.4 Uses of the Compounds

Phorbol compounds display a myriad of biological activities, including, but not limited to, tumor promotion, modulation of signal transduction pathways, activation of latent viruses, inhibition of virus entry, modulation of inflammatory responses, modulation of cell proliferation, and effects on nociception. The phorbol compounds described herein are useful in modulating any of these activities associated with phorbol compounds. Moreover, the phorbol compounds find uses in the treatment of various disorders and diseases associated with the biological activities modulated by phorbol compounds. Thus, the prodrug compounds can find applications in treating inflammatory reactions, neoplastic growth, viral infections (e.g., HIV infection), and for use as analgesics (i.e., inhibiting nociception). For embodiments involving treatment of a subject, phorbol compounds that are either non-tumor promoting or have minimal tumor promoting activity are desirable. In some embodiments, the non-tumor promoting compound can be derivatives and analogs that inhibit the tumor promoting activity of tumor promoting phorbol compounds. In this regard, phorbol compounds in which the R" of the structures disclosed herein (e.g., structure 1a; RI; R2) are lower alkanyl, lower unsubstituted alkyl, or benzyl have been shown to display minimal or no tumor promoting activity for the active compounds.

Generally, the phorbol compounds disclosed herein are prodrugs in that the compounds are converted to the active forms. This can occur through inherent instability of the prodrug moiety under a specified set of conditions or through the action of a biological process that biotransforms the prodrug to the active drug metabolite. Thus, for many of the uses herein, the phorbol compound is subjected to biological conditions that result in conversion of the prodrug compounds to the active form by removal of the progroup moiety.

The compounds can be used independently as a single agent, or in some embodiments, used in combination with other agents. These combinations include other phorbol compounds as well as other non-phorbol agents. Thus, in various embodiments, the phorbol compounds can be used adjunctively with other anti-inflammatory, anti-retroviral, anti-nociceptive, and anti-neoplastic compounds.

5.4.1 Binding and Modulation of Phorbol Receptors and Associated Signal Transduction Pathways In accordance with the above, in some aspects, the phorbol compounds can be used to modulate the activity of phorbol receptors and their corresponding signal transduction systems by contacting a phorbol receptor with the compounds disclosed herein and measuring the activity of the phorbol receptor. A phorbol receptor is any biological moiety that binds to phorbol compounds with specificity and/or affects a physiological process associated with the receptor when the binding occurs in vivo or in vitro. Compounds that bind a phorbol receptor include agonists and antagonists of other phorbol compounds or similar modulators, for example diacyglycerol. Antagonists include compounds that bind the phorbol receptor but which itself is without any direct effect on a cellular process affected by the phorbol receptor. Binding interactions can take place in crude extracts containing the receptor, or semi-purified or purified receptor preparations. Binding is readily measured with labeled phorbol compounds, such as radiolabeled phorbol compounds, which can be made during synthesis by incorporating labeled starting materials or intermediates, or by exchange reactions. Suitable radiolabels include $^3H$, $^{14}C$, $^{32}P$, $^{35}S$, $^{36}Cl$, $^{57}Co$, $^{131}I$ and $^{186}Re$. Other labeling methods will be apparent to the skilled artisan.

In some embodiments, the phorbol compounds can be used to modulate the activity of receptors protein kinase C, a family of lipid regulated serine threonine kinases that phosphorylate numerous cellular proteins. The PKC family comprises at least three subclasses of structurally related proteins, which are categorized based on their regulation. The classical PKCs (cPKCs) encompass isoforms whose activity is regulated by $Ca^{+2}$ and/or lipid diacylglycerol, and modulated by phorbol esters. Exemplary cPKCs include PKCα, β1, βII, and γ. A second class of PKCs, designated in the art as novel PKCs or nPKCs, are also activated by diacylglycerol and phorbol esters but does not require $Ca^{+2}$. Exemplary nPKCs include δ, ε, θ and η forms. The third class of PKCs, denoted in the art as atypical PKCs are not regulated by $Ca^{+2}$ and do not respond to either diacylglyercol or phorbol esters. Exemplary atypical PKCs include PKCζ and PKCτ/λ. Because the third class of PKCs appears not to interact with phorbol esters, these proteins would not be characterized as phorbol receptors.

Another group of phorbol receptors are defined by a class of proteins described as PKC related kinases. These groups of receptors are serine threonine kinases regulated by diacylglyercol and phorbol esters. Exemplary receptors of this class include PKCμ, PKD and PKRs. These kinases differ from the other PKCs with respect to substrate specificity and regulation. Forms PKCμ/PKD contain a putative transmembrane domain in the amino terminal region and a C1 region with two cyteine rich domains that bind phorbol esters, and a pleckstrin homology domain. The kinase catalytic domain is related to the kinase of $Ca^{+2}$/calmodulin dependent kinase II. This enzyme does not act on substrates typically active with other PKCs but acts on substrates phosphorylated by calmodulin dependent kinases. The second type of PKC-related kinases, referred to as PRKs, has a kinase region with homology to the kinase domain of PKCs, but appears to not bind phorbol esters or regulated by $Ca^+$. Instead, kinase activity is sensitive to phospholipids phosphatidylinositol 4,5 bisphosphate and phosphatidylinositol 3,4,5, triphosphate.

In other embodiments, the phorbol receptors are class of proteins described as "nonkinase phorbol ester/DAG receptors." These receptors include the mammalian α and β chamaerins, Ras-GRP, and *Caenorhabditis elegans* Unc-13. Nonkinase phorbol receptors are characterized by a single copy of the cysteine rich domain that appears to function in binding to diacylglycerol. The chimaerin proteins have a regulatory domain found in PKCs and BCR, and displays phorbol binding property similar to PKCα. Chimaerin do not have sequences associated with kinase activity, but have a GAP (GTPase activating protein) at the carboxy terminal region, which may function in down regulating Rac function. Another member of the non-kinase phorbol esters is RasGRP (i.e., Ras guanyl-releasing protein). RasGRP has a single cysteine rich region at the carboxy terminal domain similar to those in other PKCs, a catalytic region with sequence similarity to CDC25 box, which acts as a Ras activator, and a Ras exchange motif conserved among guanyl nucleotide releasing factors. In the RasGRP, the phorbol ester binding site may function in recruitment of RasGRP to the plasma membrane. Binding to these phorbol receptors and subsequent activation of PKC may be used to assess the activity the phorbol compounds described herein.

It is to be understood that the descriptions of phorbol receptors above reflect the state of knowledge in the art and are not intended to be limiting. Thus while some biological moieties may be currently described as not binding phorbol compounds, there may be subsequent evidence showing that such biological moieties bind to phorbol compounds, and thus would be encompassed within the description of a phorbol receptor.

Many of the PKC target substrates are components of signal transduction pathways and include proteins that regulate ion channels, calcium- and calmodulin-binding proteins, growth factor receptors, structural and regulatory proteins of the cytoskeleton, components of the transcriptional machinery, efflux pumps, and many other proteins. PKC phosphorylates serine and threonine residues on these protein targets, typically in a consensus sequence RxxS/TxRx (where x is any amino acid) (Nishikawa et al., 1997, *J. Biol. Chem.* 272:952-960). Any of the known substrates, natural or synthetic, can be used to detected phorbol mediated activation of PKC activity. Exemplary substrate targets include MARCKS, GAP43, GABA type A receptor g2L, EGF receptor, ribosomal protein S6, Troponin I, insulin receptor tyrosine kinase, c-Kit (stem cell factor receptor), annexin II, and Wiskott-Aldrich interacting protein. Exemplary synthetic substrates are described in Nishikawa et al., supra; Loog et al., 2005, *J. Biomol. Screen.* 10(4):320-328; and Toomik et al., 1997, *Biochem. J.* 322:455-460. The prodrug forms can be tested in the presence of agents capable of converting the prodrug forms to the active compounds. Exemplary agents for activation include, culture medium (conditioned or unconditioned), cell/issue homogenates, microsomal extracts, or cytosol preparations. The biological activating agents can be prepared from different organs, such as the liver or intestine, which can contain biological activities capable of biotransforming the prodrug forms.

In other embodiments, the phorbol compounds can be used to modulate, or assessed for their ability to modulate, signal transduction pathways and other cellular process dependent on phorbol receptors (e.g., PKC). By "signal transduction or cellular process dependent on phorbol receptors" is meant any signal transduction process that is modulated, whole or in part, by binding of phorbol compounds to receptors such as the PKC isoforms. Modulation refers to activation or inhibition of the signal transduction process, and can be detected by examining the cellular products or cellular states affected by phorbol receptor activation. Processes regulated by phorbol receptor activity include, by way of example and not limitation, cell adhesion, ion channel activity (e.g., calcium, sodium, and potassium channels), neurotransmitter transporters, transcriptional regulation, hormone activity, and synaptic plasticity. Thus, in some embodiments, the phorbol compounds can be used to modulate or assess transcription dependent on phorbol receptors. Promoters containing TPA responsive element (TRE) and serum responsive element (SRE) are known to be regulated by PKC activation. For instance, activation of PKCγ leads to dephosphorylation of c-Jun, a transcription regulator, which binds to TRE sequences to activate expression of the TRE regulated gene product. PKC appears to mediate this effect by stimulating dephosphorylation of glycogen synthase kinase-3β (GSK-3β), ultimately leading to dephosphorylation of c-Jun and thereby affecting its interaction with c-fos to modulate promoter activity. Gene products modulated via TRE containing genes include, as non-limiting examples, collagenase, stromelysin, and metallothionein IIA.

Transcriptional modulation of SRE containing promoters appears to occur through involvement of PKC in the MAP kinase pathway involving ERK (extracellular receptor kinase), which is activated by a number of growth factor receptors. Binding of growth factors to their cognate receptors results in activation of PKC, which in turn phosphorylates Raf, a modulator or ERK activity. Raf is also activated by Ras, which is also activated by growth factors. Thus, PKC appears to supplement the activation of Raf that occurs via Ras activity. Activated ERK modulates the activity of SRE containing promoters by modifying TCF, a transcription factor that interacts with SRF (serum response factor) to bind to SRE sites. One consequence of increased SRE promoter activity is transcription of c-fos, a gene product involved in tumorigenesis. Thus, the JNK and RAF signaling pathways are modulated by phorbol esters, and thus comprise phorbol receptor dependent pathways.

An effect of the binding of phorbol esters to PKC is the translocation of the PKC protein from the cytosol to the membrane. Binding of natural ligand diacylglycerol or phorbol compounds to the C1 region of certain PKCs in the presence of $Ca^{+2}$ appears to make the C1 region more hydrophobic, and coupled with other conformational changes in the membrane, increases its affinity for the cell membrane. The result is translocation of the PKC from the cytosol to the membrane, a transition readily detected using labeled PKC proteins (see, e.g., Sakai et al., 1997, *J Cell Biol.* 139(6):1465-76). In these assays, binding of active phorbol esters (i.e., phorbol compounds that stimulate PKC activity) induces translocation while inactive phorbol esters (i.e., phorbol compounds that do not stimulate PKC activity) do not induce translocation. Translocation with various lipid ligands and phorbol esters are described for various PKC subtypes, such as PKCγ, PKCα, PKCξ and PKCδ (see, e.g., Seki et al., 2005, *Genes to Cells* 10:225-239). Thus, the phorbol compounds can also be tested for effect of signal transduction pathways by contacting cells with the phorbol compounds under biological conditions that result in removal of the progroup and determining the intracellular translocation of PKC enzymes.

It is to be understood that the pathways described above are exemplary of signal transduction pathways dependent on phorbol receptors. Other pathways will be apparent to the skilled artisan, and can serve as useful targets for the phorbol compounds herein as well as providing assays for assessing phorbol activity. As noted above, phorbol activity includes antagonistic as well as agonistic activity against various phorbol receptors and signal transduction pathways dependent on phorbol receptor activity.

5.4.2 Active Tumor Promoters and Tumor Promoter Inhibitors.

In various embodiments, the phorbol compounds find uses as tumor promoters that accelerate the tumor forming ability of various carcinogens when administered in combination to a host. Phorbol esters were originally identified based on their tumor promoting ability, a characteristic thought to be related to activation of PKC signaling pathways and induction of inflammatory reactions. Classically, tumor promoting activity assays involve topically applying the skin of a host animal host a tumor initiator (e.g., carcinogen such as 7,12-dimethylbenz(a)anthracene). This is followed by administration of the tumor promoter compound (e.g., phorbol compound), either orally or topically. Formation of skin tumors are assessed visually as well as histologically. Control groups, for example, treatment of tumor promoter alone or initiator alone, are used to determine the activity of the tumor promoter. Known tumor promoting phorbol compounds, such as 12-O-tetradecanoylphorbol 13-acetate (TPA), serve as useful reference compounds in assessing tumor promoting potential. Where the effect is inhibiting tumor promotion, the phorbol compound under study can be used in combination with a known tumor promoter. For instance, in the skin test, tumorigenesis is initiated by applying the tumor initiator. This is followed by administration of the phorbol compound in combination with, simultaneously or sequentially, a known tumor promoter such as TPA.

Other in vivo assays for tumor promoting activity have been developed based on other characteristics of tumor formation. In some embodiments, the tumor promotion assay can use the ability of tumor promoters to induce angiogenesis in animal model systems (see, e.g., Morris et al., 1988, *Am J*

*Physiol.* 254(2):C318-22). Active tumor promoters appear to stimulate angiogenesis while inactive tumor promoters do not stimulate angiogenesis. Thus, determining whether a phorbol compound promotes angiogenesis provides another basis to assess the tumor promoting or tumor promoter inhibiting activity.

In addition to in vivo systems, various in vitro based systems are available for assessing tumor promoting activity. In some embodiments, the in vitro assessment comprises contacting cultured cell lines that respond to treatment with phorbol compounds with the phorbol compounds herein, and measuring a cellular reaction to the compound. Depending on the cell type, cellular responses include, among others, stimulation of proliferation of quiescent cells, inhibition of cell proliferation, and stimulation of terminal differentiation. Cultured cells that respond to phorbol compounds by proliferating include as non-limiting examples, 3T3 mouse fibroblasts (Rosengurt, E., 1986, *Science* 234:161-166) and resting T lymphocytes (Berry et al., 1990, *Eur. J Biochem* 189:205-214). Cultured cells that stop proliferating and undergo differentiation in response to phorbol compound include as non-limiting examples HL-60 promyelocytic leukemia cell line, human T-lymphoblastic cell line MOLT-3, and B cell Daudi cells. In these embodiments, various assays can be used to assess cell proliferation. These include, as non-limiting examples, incorporation of labeled DNA synthesis substrates (e.g., $^3$H labeled dNTP or digoxigenin-labeled dUTP), and labeling with DNA specific dyes coupled with analysis in a fluorescence activated cell sorter. Other methods will be apparent to the skilled artisan.

5.4.3 Activation of Latent Viruses and Antiviral Activities: Treatment of Viral Infections.

In some aspects, the compounds find use in attenuating or inhibiting viral activity. For purposes of treatment, a subject afflicted with a viral infection can be administered an amount of the phorbol compounds effective to treat the viral infection. An anti-viral effect includes any effect that attenuates or inhibits viral activity and is not limited to any mechanism of action. Thus, the anti-viral compound or composition can modulate, among others, viral entry into the cell, viral replication, viral production, and virus stability. An "anti-viral compound" refers to a compound or compositions that attenuates or inhibits viral infection.

Various phorbol compounds display anti-viral properties and display the ability to activate latent viruses. "Viral latency" refers to the persistence of a virus in non-infectious form and typically occurs where the virus infects the host without cytopathic effect followed by long term maintenance of the viral genome in the host cell. Some of the mechanisms for initiation of latency include, among others, infection of non-permissive cells, presence of conditions affecting the cytopathic process, or the production of viral variants. Examples of nonpermissive infections are Epstein Barr Virus (EBV) infection of B lymphocytes, HIV infection of mononuclear phagocytes, cytomegalovirus (CMV) infection of peripheral blood mononuclear cells (PMBC), and herpes simplex virus (HSV) infection of sensory neurons. Infection of the specified cell types by the corresponding virus results in little or no expression of viral gene products and thus no or insignificant production of infectious viral particles.

Maintenance of the viral genome in the latency phase depends on the virus type. Viruses that integrate into the host genome are replicated along with the host chromosome, maintenance being part of host cell division process. Retroviruses, such as HIV, propagate the viral genome by converting the RNA into a DNA copy, which is then integrated into the host cell genome. Other viruses are maintained episomally, where viral replication is intimately connected to the host cell cycle but controlled by virally expressed proteins. EBV and papillomaviruses are examples of viruses that exist episomally during the latency period. Still other viruses exist episomally but without replication of the viral genome. An example of this latter mechanism is persistence of HSV in sensory neurons. HSV initially infects the oral mucosa and then enters the sensory nerve endings to establish a latent infection. The limited expression of certain HSV viral gene products (e.g., IE gene) limits the production of infectious viral particles. Since sensory neurons do not replicate, there is no requirement for replication of the HSV viral genome for maintenance. There is no loss of the virus by dilution as might occur if the virus infects actively dividing cells.

Under some conditions, latent viruses undergo reactivation, a process resulting in production of viral particles from the cell harboring the latent virus. Phorbol compounds, such as phorbol esters and 12-deoxyphorbol 13-acetate, have the ability to reactivate latent viruses. Non-limiting examples of viruses showing latency include human T cell leukemia virus type I (HTLVI) (Lin et al., 2005, *Virology*. June 15: Epub); human immunodeficiency virus (HIV) (Korin et al., 2002, *J. Virol.* 76(16):8118-23); Kulkosky et al., 2001, *Blood*. 98(10): 3006-15), and Epstein Barr Virsu (EBV) (Davies et al., 1991, *J. Virol.* 65:6838-6844). Although, the mechanism of reactivation appears to vary between viruses, the mechanistic aspects are not critical for these applications, and the compounds find a number of different uses based on reactivation activity of the phorbol compounds.

In some embodiments, the reactivation of latent viruses is used as a diagnostic test to determine the viral reservoir residing in a subject or a cell preparation. The method comprises contacting cells harboring a latent virus with an amount of phorbol compound effective to reactivate the virus. Virus reactivation can be detected by various techniques, such as polymerase chain reaction, viral plaque assays, or virus specific antibodies. Determining the levels of latent viruses can provide a measure of the effectiveness of a specific viral therapy or provide information useful in determining the effectiveness of other therapies used to reduce the viral reservoir. In other embodiments, as further described below, the reactivation properties are used as adjunctive therapy in combination with other antiviral agents for reducing viral reservoirs or eliminating presence of the virus in an infected subject. For example, prostratin appears to reactive latent HIV virus but without affecting the effectiveness of highly active antiretroviral therapy (HAART) (Kulkosky et al., supra). HAART is a combination drug therapy (e.g., drug cocktail) using reverse transcriptase and protease inhibitors to provide different modes of inhibiting the virus. It is a highly effective treatment for reducing viral load and maintaining the infection in a chronic state. Treatments can comprise administering to a chronically infected subject a phorbol compound displaying reactivating properties to induce the latent viruses, and adjunctively administering an anti-viral compound, such as a combination of the compounds used in HAART therapy (Kulkosky et al., supra).

In other embodiments, the phorbol compounds can be used to treat a viral infection by administering to a subject infected with the virus an amount of the phorbol compound effective to treat the viral infection. This use is based on the anti-viral activities of some phorbol compounds. For instance prostratin inhibits the cytopathic activity of HIV and also inhibits the entry of the virus into a cell (Witvrouw et al., supra). Erickson et al., 1995, *J Nat. Products* 58(5):769-72 describes anti-viral activities of 12-deoxyphorbol 13-(3E,5E-decadienoate). The mechanism of the inhibition is not critical to the uses herein but can involve reduction in levels of the natural cellular receptor for HIV, coreceptors CCR5 and CXCR4 (Rullas et al., *Antiviral Ther.* 9:545-554). In addition to their use in the treatment of viral infections, the compounds herein can also be used as a prophylactic measure to reduce the probability of infection by the virus in an uninfected subject.

As described throughout this disclosure, the phorbol compounds can be administered individually or administered in combination with other therapeutic compounds (e.g., antiviral compound), either in the form of a composition or adjunctively by simultaneous or sequential administration. Thus, for treatment of retroviral infections, the phorbol compounds can be used in combination with, among others, nucleoside reverse transcriptase inhibitors, non-nucleoside reverse transcriptase inhibitors, protease inhibitors, and virus uptake/absorption inhibitors. Anti-viral compounds that affect viral fusion or viral transcription can also be used.

Nucleoside/nucleotide reverse transcriptase inhibitors inhibit action of the viral reverse transcriptase required for conversion of the viral RNA into DNA during viral replication. Non-limiting examples of these inhibitors include azidothymidine and its derivatives (e.g., AZT, Zidovudine), $(2R^X,cis)$-4-amino-1-(2-hydroxymethyl-1-1-oxathiolan-5-yl)-(1H)-pyrimidine-2-one (i.e., Lamivudine), 2',3'-dideoxyinosine (didanosine), 2',3'-dideoxycytidine (i.e., Zalcitabine), 2',3'-didehydro-3'-deoxythymid-ine (i.e., stavudine), (1S,cis)-4-[2-amino-6-(cyclopropylamino)-9H-purin-9-1-yl]-2-cyclopentene-1-methanol sulfate (i.e., abacavir), (−)-beta-2',3'-dideoxy-5-fluoro-3'-thiacytidine (i.e., emtricitabine), and phosphonate 9-R-(2-phosphonomethoxypropyl)adenine (i.e., PMPA; tenofovir disoproxil fumarate; adefovir) and various derivatives thereof (see, e.g., Deeks et al., 1998, *Antimicrob. Agents Chemother.* 42(9):2380-2384).

Non-nucleoside reverse transcriptase inhibitors (NNRTI) are antiviral compounds that inhibit the action of viral reverse transcriptase by binding to the enzyme and disrupting its catalytic activity. Non-limiting examples of inhibitors of this class include 11-cyclopropyl-5,11-dihydro-4-methyl-6H-dipyrido-[3,3-b-2',3'-][1,4]diazepin-6-one (i.e., Nevirapine); piperazine, 1-[3-[(1-methyl-ethyl)amino]-2-pyridinyl]-4-[[5-[(methylsulfonyl)amino]-1-H-indol-2-yl]carbonyl]-, monomethane sulfonate (i.e., Delavirdine); and (S)-6-chloro-4-(cyclopropylethynyl)-1,4-dihydro-4-(trifluoromethyl)-2H-3,-1-benzoxazine-2-one (i.e., Efavirenz). Other include quinazolinone and its derivatives, for example trifluoromethyl-containing quinazolin-2(1H)-ones (Corbett et al., 2000, *Prog. Med. Chem.* 40:63-105; calanolide A (Newman et al., 1998, *J Pharm. Sci.* 87(9):1077-1080; and 6-arylmethyl-1-(ethoxymethyl)-5-alkyluracil (i.e., emivirine) and its analogs (El-Brollosy, 2002, *J Med. Chem.* 45(26):5721-5726).

In other embodiments, the combination treatment is with protease inhibitors, which typically target the HIV protease enzyme, a 99-amino acid homodimer that cleaves pol-gag polypeptides on the viral envelope. Inhibition of the HIV protease results in release of immature, noninfectious viral particles. In addition, many of the protease inhibitors can also exert additional antiviral effects by inhibiting cellular proteasome function. Non-limiting examples of protease inhibitors useful in the methods herein include indinavir, saquinavir (fortovase), ritonavir, nelfinavir, amprenavir, and lopinavir.

As noted above, HAART is a drug regimen consisting of at least three different anti-retroviral drugs and is shown to be effective therapy for controlling viral infection and limiting the cytopathic effects of the virus such that a chronically infected state is established in the infected subject. In the adjunctive therapies, various combinations of anti-retroviral agents can be used together with the phorbol compounds disclosed herein.

In the embodiments herein, various assays can be used to examine the anti-viral activity of the phorbol compounds. For instance, HIV viral replication is measurable by assessing the activity of reverse transcriptase or the production of viral particles by infected cells. Reverse transcriptase measurements can be any standard assays (see, e.g., Buckheit et al., 1991, *AIDS Research and Human Retroviruses* 7:295-302), such as an assay using labeled nucleotide triphosphates and measuring incorporation of label into nucleic acid. Determining the presence of viral particles can be based on nucleic acid amplification reactions (e.g., PCR) using viral specific primers or hybridization reactions (e.g., microarray detection systems). Antibodies directed against viral specific proteins, such as capsid protein p24, are useful in measuring the presence of viral particles. Other methods will be apparent to the skilled artisan.

Although illustrations above are for HIV, it will be apparent to the skilled artisan that analogous assays can be used for other types of virus. Further, it is to be understood that because the exact mechanism by which phorbol compounds exert their anti-viral activity is unclear, negative results with some assays directed to specific aspects of viral pathogenecity or negative results using certain cell types can not be indicative of the efficacy of the compounds.

In further embodiments, the phorbol compounds disclosed herein can be used in combination with non-retroviral anti-viral compounds. Combinations with non-retroviral anti-viral compounds can be applicable where the phorbol compound is used to reactivate latent viruses to eliminate or reduce the reservoir of virus in an infected host. The type of non-retroviral anti-viral compound chosen will depend on the type of virus present in the infected host. In some embodiments, the anti-viral compound chosen for the combination comprises an agent effective against DNA viruses. In other embodiments, the anti-viral compound chosen for the combination comprises an agent effective against non-retroviral RNA viruses. Exemplary anti-viral agents include, by way of example and not limitation, acyclovir, valacyclovir, docosanol famciclovir, forcarnet, formivirsen, gangciclovir, idoxuridine, penciclovir, trifluridine, valacyclovir, vidarabine, amantadine, oseltamivir, rimantidine, zanamivir, fomivirsen, imiquimod, lamivudine, and ribavirin. Other anti-viral compounds for use with the phorbol compounds disclosed herein will be apparent to the skilled artisan.

5.5 Uses as Anti-Neoplastic and Anti-Inflammatory Agents and as Analgesics

In some aspects, the phorbol compounds can be used to treat various cell proliferative disorders by administering to a subject afflicted with a cell proliferative disorder an amount of the phorbol compound effective to treat the cell proliferative disorder. As used herein, a "cell proliferative disorder" refers to a condition or disease in which normal controls that regulate cell division are abnormal, thereby resulting in abnormal cell proliferation. Cell proliferative disorder includes neoplasms or tumors, which generally relate to abnormal growth of tissues.

Anti-neoplastic activity of certain phorbol compounds have been demonstrated against leukemia, carcinoma, and melanoma (see, e.g., U.S. Pat. Nos. 6,063,814; 5,643,948). Cytotoxicity of 12-dexoxyphorbol compounds against cancer cell lines are described in Fatope et al., 1996, *J Med. Chem.* 39(4):1005-8. Because of the effectiveness phorbol compounds against diverse types of tumors, it has been suggested that non-tumor promoting compounds with anti-neoplastic activity can be effective against many different types of cancers. Cancers are traditionally classified based on the tissue and cell type from which the cancer cells originate. Carcinomas are considered as cancers arising from epithelial cells while sarcomas are considered as cancers arising from connective tissues or muscle. Other cancer types include leukemias, which arise from hematopoietic cells, and cancers of nervous system cells, which arise from neural tissue. For non-invasive tumors, adenomas are considered as benign epithelial tumors with glandular organization while chondromas are benign tumor arising from cartilage. In the present disclosure, the compounds can be used to treat proliferative disorders encompassed by carcinomas, sarcomas, leukemias, neural cell tumors, and non-invasive tumors.

In some embodiments, the compounds can be used to treat solid tumors arising from various tissue types, including, but not limited to, cancers of the bone, breast, respiratory tract, brain, reproductive organs, digestive tract, urinary tract (e.g., bladder), eye, liver, skin, head, neck, thyroid, parathyroid, and mestastatic forms thereof. Proliferative disorders of the hematopoietic system that can be treated include, but are not limited to, various T cell and B cell lymphomas, non-Hodgkins lymphoma, cutaneous T cell lymphoma, Hodgkins disease, and leukemias (e.g., acute myeloid leukemia, acute lymphoblastic leukemia, chronic lymphocytic leukemia, chronic myelogenous leukemia, etc.).

As noted previously, for use of the phorbol compounds in a therapeutic setting, prodrug forms of the compounds that are non-tumor promoting are desirable. Non-tumor promoting compounds include, by way of example and not limitation, 12-deoxyphorbol 13-acetate, 12-deoxyphorbol 13-propanoate, and 12-deoxyphorbol 13-phenylacetate. These phorbol compounds bind to and activate protein kinase C but do not produce the typical tumor promoting effects (e.g., hyperplasia) of other phorbol esters (e.g., TPA), or induce only a partial response (e.g., inflammation). Pretreatment with these agents inhibits the tumor promoting effect of various tumor promoting phorbol esters (Szallasi et al., 1993, *Cancer Res.* 53(11):2507-12).

In some embodiments, the phorbol compounds can be used in combination with other cancer chemotherapeutic agents. For instance, U.S. Pat. No. 6,063,814 describes the use of TPA in combination with cytotoxic agent araC (cytosine arabinoside) and shows a synergistic anti-proliferative effect of the combination. Anti-tumor responses were also observed in patients previously treated with hydroxyurea or bisulfan. Thus, for treating various cell proliferative disorders, various anti-neoplastic agents can be used in combination with the phorbol compounds disclosed herein, either in the form of a composition or by adjunctive administration. Various classes of anti-neoplastic compounds suitable for the uses herein include, but are not limited to, alkylating agents, antimetabolites, vinca alkyloids, taxanes, antibiotics, enzymes, cytokines, platinum coordination complexes, and substituted ureas. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil and cytosine arbinoside; and purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as anti-neoplastic agent is L-asparaginase. Exemplary coordination compounds include, by way of example and not limitation, cisplatin and carboplatin. These and other useful anti-cancer compounds are described in Merck Index, 13th Ed. (O'Neil M. J. et al., ed) Merck Publishing Group (2001) and *Goodman and Gilmans The Pharmacological Basis of Therapeutics,* 10th Edition, Hardman, J. G. and Limbird, L. E. eds., pg. 1381-1287, McGraw Hill, (1996), both of which are incorporated by reference herein.

In other aspects, the analogs and derivatives can be used to attenuate or inhibit an inflammatory reaction. Anti-inflammatory activities of certain phorbol compounds are described in U.S. Pat. No. 5,643,948 and Ma et al., 1997, *Phytochemistry* 44(4), 663-666. The phorbol compounds can be administered to a subject with an inflammatory reaction in an amount sufficient to attenuate or inhibit the inflammatory reaction. In these embodiments, the phorbol compounds can be use alone or in combination with other anti-inflammatory compounds, such as non-steroidal anti-inflammatory drugs (NSAID). In some embodiments, the anti-flammatory compounds can be Cox-1 and/or Cox-2 inhibitors. Non-limiting examples of such anti-inflammatory compounds include, among others, aspirin, acetoaminophen, ibuprofen, diclofenac, and refocoxib. Others anti-inflammatory compounds suitable for the combinations herein will be apparent to the skilled artisan.

In further aspects, the phorbol compounds can be used as analgesics. As used herein, "analgesic" refers to reduction or relief of pain. Analgesic effect of compound prostratin is described in Ma et al., 1997, *Phytochemistry* 44(4), 663-666. The compounds can be administered to a subject afflicted with pain an effective amount of the phorbol compound in an amount sufficient to reduce or relieve the pain. Pain refers to an unpleasant sensory and emotional experience associated with actual or potential tissue damage generally resulting from the stimulation of specialized nerve endings. Pain may be contained to a localized area, as in an injury, or it can be a more diffuse through the subject. Pain may arise from any condition, such as physical injury, disease, or emotional disorder.

Various experimental tests can be used to determine the effectiveness of the compounds for treating pain. Art recognized tests include, among others, tail flick test or hot plate tests. These tests entail exposing the tail of a test animal, typically a mouse or rat to a noxious thermal stimulus and measuring the time the animal flicks its tail in response to the stimulus. An analgesic effect is indicated where there is an increase in the time in which the tail flick response occurs. Other types of unpleasant test stimuli for measuring pain response and tolerance to pain include, among others, electrical, mechanical, and chemical stimuli (see, e.g., Le Bars et al., 2001, *Pharmacological Reviews* 53(4):597-652). The stimuli may be short in duration, and can be applied with variable frequency to test responses to acute pain. Eliciting longer duration pain typically involves intradermal, intraperitoneal, intra-arterial, or intradental administration of irritating chemical agents, such as formalin and phenylbenzoquinone.

For purposes of treatment, the compound can be administered locally to the pain site, or administered systemically to a subject in an amount effective to reduce or eliminate the pain. In other embodiments, the compounds can be administered prophylactically to prevent the occurrence or recurrence of pain in the subject. The compounds can be administered one more times a day until sufficient relief or reduction in pain is obtained by the subject.

5.6 Pharmaceutical Compositions and Administration

When used for treatment of various disorders or conditions, the phorbol compounds can be administered singly, as mixtures of one or more active compounds or in a mixture or combination with other agents useful for treating such diseases and/or symptoms associated with such diseases. The active compounds can be administered per se or as pharmaceutical compositions. For pharmaceutical compositions, the phorbol compounds can be formulated with a pharmaceutically acceptable vehicle. A "pharmaceutically acceptable vehicle" refers to a diluent, adjuvant, excipient or carrier with which the compound is administered.

The composition can be made into a pharmaceutical formulation that is compatible with its intended route of administration. Examples of routes of administration include parenteral, e.g., intravenous, intradermal, subcutaneous, oral (e.g., inhalation), transdermal (topical), transmucosal, rectal and oral administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The pharmaceutical formulations can be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical formulations can be formulated in a conventional manner using one or more physiologically acceptable carriers, which can be selected from excipients and auxiliaries that facilitate processing of the active compounds into preparations which can be used pharmaceutically.

A variety of pharmaceutical forms can be employed. Thus, if a solid carrier is used, the preparation can be tableted, placed in a hard gelatin capsule in powder or pellet form, or in the form of a troche or lozenge. The amount of solid carrier can vary, but generally will be from about 25 mg to about 1 gm. If a liquid carrier is used, the preparation will be in the form of syrup, emulsion, soft gelatin capsule, sterile injectable solution or suspension in an ampoule or vial or non-aqueous liquid suspension.

In some embodiments, to obtain a stable water-soluble dose form, a pharmaceutically acceptable salt of compound can be dissolved in an aqueous solution of an organic or inorganic acid, such as 0.3M solution of succinic acid or citric acid. If a soluble salt form is not available, the agent can be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from about 0% to about 60% of the total volume.

In other embodiments, the pharmaceutical formulation can also be in the form of a solution of a salt form of the active ingredient in an appropriate aqueous vehicle such as water or isotonic saline or dextrose solution.

Formulation can be based upon the route of administration chosen. For injection, the compounds can be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining with pharmaceutically acceptable carriers known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, and sorbitol; cellulose preparations, for example, maize starch, wheat starch, rice starch, potato starch, gelatin, gum, methyl cellulose, hydroxypropylmethyl-cellulose, sodium carboxymethylcellulose; or polyvinylpyrrolidone (PVP). If desired, disintegrating agents can be added, such as crosslinked polyvinyl pyrrolidone, agar, or alginic acid or a salt thereof such as sodium alginate.

Dragee cores can be provided with suitable coatings. For this purpose, concentrated sugar solutions can be used, which can optionally comprise gum horoi, polyvinyl pyrrolidone, Carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compounds and agents.

Pharmaceutical forms which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the formulations can take the form of tablets or lozenges formulated in a conventional manner.

Oral formulations generally include an inert diluent or an edible carrier. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. Some embodiments of oral formulations include microcrystalline tablets, gelatin capsules, and the like.

For administration intranasally or by inhalation, the compounds can be conveniently delivered in the form of an aerosol spray presented from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of gelatin for use in an inhaler or insufflator and the like can be formulated comprising a powder mix of the compound and a suitable powder base such as lactose or starch.

In other embodiments, the compounds can be formulated for parenteral administration by injection, e.g., by bolus injection or continuous infusion. Formulations for injection can be presented in unit-dosage form, e.g., in ampoules or in multi-dose containers, with an added preservative. The parenteral formulations can take such forms as suspensions, solutions or emulsions in oily or aqueous vehicles, and can comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions can comprise substances which increase the viscosity of the suspension, such as sodium carboxymethyl cellulose, sorbitol, or dextran. Optionally, the suspension can also comprise suitable stabilizers or agents which increase the solubility of the compounds to allow for the preparation of highly concentrated solutions. Additionally, suspensions of the active agents can be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). The composition should be sterile and be fluid to the extent that easy syringability exists. It should be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid horoidsene glycol, and the like), and suitable mixtures thereof. The proper fluidity can be maintained, for example, by the use of a coating such as lecithin, by the maintenance of the required particle size in the case of dispersion and by the use of surfactants. Prevention of microbial growth can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of at least one compound disclosed herein in an appropriate solvent with one or a combination of ingredients enumerated above, as required, followed by filtered sterilization. Generally, dispersions can be prepared by incorporating the compound into a sterile vehicle that comprises a basic dispersion medium and the required other ingredients from those enumerated above. In the case of sterile powders for the preparation of sterile injectable solutions, suitable methods of preparation include vacuum drying and freeze-drying, which yields a powder of the active compound plus any additional desired ingredient from a previously sterile-filtered solution thereof.

Systemic administration can also be by transmucosal or transdermal means. In some embodiments, penetrants appropriate to the barrier to be permeated are used in the formulation. Such penetrants are generally known in the art, and include, but are not limited to, detergents, bile salts, and fusidic acid derivatives. Transmucosal administration can be accomplished through the use of nasal sprays or suppositories. For transdermal administration, the active compounds can be formulated into ointments, salves, gels, foams, powders, sprays, aerosols or creams as generally known in the art.

For example, for topical formulations, pharmaceutically acceptable excipients or cosmetically acceptable carriers and additives include solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include, among others, glycerin and sorbitol. Suitable emulsifiers include, among others, glyceryl monostearate, glyceryl monoleate, stearic acid, polyoxyethylene cetyl ether, polyoxyethylene cetostearyl ether, polyoxyethylene stearyl ether, polyethylene glycol stearate, and propylene glycol stearate. Suitable pH agents include, among others, hydrochloric acid, phosphoric acid, diethanolamine, triethanolamine, sodium hydroxide, monobasic sodium phosphate, dibasic sodium phosphate. Suitable preservatives include benzyl alcohol, sodium benzoate, parabens, and others known in the art.

For administration to the eye, the compounds herein can be delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, retina and sclera. The pharmaceutically acceptable ophthalmic vehicle can be an ointment or an encapsulating material. Compounds can also be injected directly into the vitreous and aqueous humor.

In various embodiments, compounds can be in powder form for reconstitution with a suitable vehicle, e.g., sterile pyrogen-free water, before use. The compounds can also be formulated in rectal compositions such as suppositories or retention enemas, e.g., comprising conventional suppository bases such as cocoa butter or other glycerides.

In addition to the formulations described above, compounds can also be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (e.g., an emulsion in an acceptable oil) or ion-exchange resins, or as sparingly soluble derivatives, for example, as a sparingly soluble salt.

In some embodiments, a pharmaceutical carrier for hydrophobic compounds is a cosolvent system comprising benzyl alcohol, a nonpolar surfactant, a water-miscible organic polymer, and an aqueous phase. The cosolvent system can be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. In various embodiments, he proportions of a co-solvent system can be varied considerably without destroying its solubility and toxicity characteristics. Furthermore, the identity of the co-solvent components can be varied. For example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can be substituted for dextrose.

In some embodiments, other delivery systems for hydrophobic pharmaceutical formulations can be employed. Liposomes and emulsions are known examples of delivery vehicles or carriers for hydrophobic drugs and cosmetics. Certain organic solvents such as dimethylsulfoxide also can be employed, although usually at the cost of greater toxicity. Additionally, the compounds can be delivered using a sustained-release system, such as semipermeable matrices of solid hydrophobic polymers comprising the therapeutic agent. Various sustained-release materials have been established and are known by those skilled in the art. Sustained-release capsules can, depending on their chemical nature, release the compounds for a few weeks up to over 100 days.

The pharmaceutical formulations also can comprise suitable solid- or gel-phase carriers or excipients. Examples of such carriers or excipients include calcium carbonate, calcium phosphate, sugars, starches, cellulose derivatives, gelatin, and polymers such as polyethylene glycols.

In some embodiments, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

It is generally advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the compounds are dictated by and directly dependent on the unique characteristics of the active compound and the particular therapeutic effect to be achieved, and the limitations inherent in the art of compounding such an active compound for the treatment of individuals.

5.7 Dosages

The active compound(s) or compositions thereof can generally be used in an amount effective to treat or prevent the particular disease being treated. The compound(s) can be administered therapeutically to achieve therapeutic benefit or prophylactically to achieve prophylactic benefit. By "therapeutic benefit" is meant eradication or amelioration of the underlying disorder being treated, e.g., eradication or amelioration of the HIV infection, neoplastic disease, inflammation, and/or eradication or amelioration of one or more of the symptoms associated with the underlying disorder such that the patient reports an improvement in feeling or condition, notwithstanding that the patient can still be afflicted with the underlying disorder. For example, administration of an active compound to a subject suffering from HIV infection provides therapeutic benefit not only when the underlying HIV infection is eradicated or ameliorated, but also when the patient reports a decrease in the severity or duration of the symptoms associated with HIV. Therapeutic benefit also includes halting or slowing the progression of the disease, regardless of whether improvement is realized.

For prophylactic administration, the active compound can be administered to a patient at risk of developing the specified disorder or disease. For example, if a subject is suspected of being infected with HIV, the active compound can be administered to prevent infection before tests sensitive enough to detect presence of the virus can be used. Active compounds can also be administered prophylactically to healthy individuals who are at high risk of being infected by HIV (e.g., high-risk sexual activity, illicit intravenous drug abusers, HIV health workers, etc.).

The amount of active compound(s) administered will take into consideration a variety of factors, including, for example, the particular indication being treated, the mode of administration, whether the desired benefit is prophylactic or therapeutic, the severity of the indication being treated, the age, weight and sex of the patient, and the bioavailability of the particular active compound. Determination of an effective dosage is well within the capabilities of those skilled in the art.

Initial dosages can be estimated initially from in vitro assays. For example, an initial dosage for use in animals can be formulated to achieve a circulating blood or serum concentration of active compound that inhibits about 50% of HIV viral replication as measured in an in vitro assay. In other embodiments, an initial dosage for use in animals can be formulated to achieve a circulating blood or serum concentration of active compound that is equal to or greater than the $IC_{50}$ of a in vivo model of HIV infection. Such in vivo models can be primate models for HIV infection (see, e.g., Vodros et al., 2004, *Acta Microbiol Immunol Hung.* 51(1-2):1-29).

Calculating dosages to achieve such circulating blood or serum concentrations, taking into account the bioavailability of the particular active compound, is well within the capabilities of skilled artisans. For guidance, the reader is referred to Fingl and Woodbury, "General Principles," In: *The Pharmaceutical Basis of Therapeutics*, Chapter 1, pp. 1-46, 1975, and the references cited therein.

In some embodiments, the active compound(s) will provide therapeutic or prophylactic benefit without causing substantial toxicity. Toxicity of the active compound(s) can be determined using standard pharmaceutical procedures. The dose ratio between toxic and therapeutic (or prophylactic) effect is the therapeutic index. Active compound(s) that exhibit high therapeutic indices are preferred.

Dosage amounts can typically be in the range of from about 0.1 mg/kg/day to about 1.0 mg/kg/day, 1.5 mg/kg/day, 2.0 mg/kg/day, 2.5 mg/kg/day or 10.0 mg/kg/day, but can be higher or lower, depending upon, among other factors, the activity of the compound, its bioavailability, the mode of administration and various factors discussed above. Dosage amount and interval can be adjusted individually to provide plasma levels of the active compound(s) that are sufficient to maintain therapeutic or prophylactic effect. In cases of local administration or selective uptake, such as local topical administration, the effective local concentration of active compound(s) may not be related to plasma concentration. Optimize effective local dosages are well within the skill of those in the art.

In some embodiments, the compound(s) can be administered once per day, a few or several times per day, or even multiple times per day, depending upon, among other things, the indication being treated and the judgment of the prescribing physician.

5.8 Kits

The present disclosure also provides the compounds and compositions disclosed herein in the form of a kit or packaged formulation. A kit or packaged formulation can include one or more dosages of the prodrug phorbol compound, or salts and hydrates thereof. In some embodiments, the kit further comprises one or more therapeutic agents used adjunctively with the phorbol compounds in the treatment of a disorder or disease condition. For instance, the additional therapeutic agent can be an anti-retroviral agent provided in dosage forms, such as pills or capsules packaged into dispensers or blister packs, together with instructions for simultaneous or sequential administration of the therapeutic agents. In other embodiments, the package can contain the phorbol compound along with a pharmaceutical carrier combined in the form of a powder for mixing in an aqueous solution, which can be ingested by a subject. Another example of packaged drug is a preloaded pressure syringe so that the compositions can be delivered orally or intravenously in measured doses. The package or kit also includes appropriate instructions, which encompasses diagrams, recordings (e.g., audio, video, compact disc), and computer programs providing directions for use of the mono- or combination therapy.

6. EXAMPLES

6.1 Example 1

Synthesis of Prostratin Succinate (SA-101B)

Prostratin (1390 mg, 1 mmol) and succinic anhydride (120 mg, 1.2 mmol) were dissolved in dichloromethane (20 ml). DMAP (dimethylaminopyridine) at 50 mg was added under stirring and then stirred at room temperature for overnight. The solvent was evaporated and the residue subjected to chromatography on silica gel column (50 mg) with gradient of petroleum ether (60-90° C.) and acetone as eluent to give a fraction of pure prostratin succinate (Scheme (1), product 1) and another fraction containing a mixture of prostratin and prostratin succinate.

EIMS m/z: 490 ($M^+$, 2%), 472 ($M^+$-$H_2O$, 25%), 312 ($M^+$-$H_2O$—HOAc-HOSuc, 100%), 294 ($M^+$-$2H_2O$—HOAc-HO-Suc, 94%). $^1$H-NMR δ (DMCO): 0.81 (3H, d, J=6.0, H-18), 0.84 (1H, d, J=5.4, H-14), 0.98 (3H, s, H-17), 1.10 (3H, s, H-16), 1.48 (1H, dd, J=8.5, 13.2, H-12a), 1.63 (3H, dd, J=1.1; 2.8, H-19), 1.98 (3H, s, H-22), 1.98 (1H, m, H-12b), 2.32 (1H, d, J=19.5, H-11), 2.48 (1H, br. H-5), 2.48 (4H, br. H-24, 25), 3.01 (1H, t, J=5.2, H-8), 3.11 (1H, t, J=2.5, H-10), 4.39, 4.47 (2H, AB, J=12.1, H-20), 5.65 (1H, d, J=3.9, H-7), 6.98 (1H, d, J=7.4, H-1), 8.15 (1H, d, J=7.4, H-26).

6.2 Example 2

Prostratin Succinate Sodium (SA-101NB)

Prostratin succinate (2340 mg, 0.69 mmol) was added proportionately to a water solution of sodium bicarbonate (58 mg, 0.69 mmol) under stirring at room temperature and then continuously stirred for another two hours. The solution was frozen and subjected to lyophilization to yield an offwhite powder, which is the sodium salt of product (1) of Scheme (1).

$^1$H-NMR δ ($D_2O$): 0.74 (3H, d, J=6.6, H-18), 0.82 (1H, d, J=6.2, H-14), 0.86 (3H, s, H-17), 0.96 (3H, s, H-16), 1.38 (1H, dd, J=2.5; 3.8, H-12a), 1.58 (3H, s, H-19), 1.69 (1H, m, H-11), 1.92 (3H, s, H-22), 2.03 (1H, dd, J=7.2; 15.2, H-12b), 2.50 (3H, m, H-5, 24), 2.37 (2H, m, H-25), 2.72 (1H, t, J=5.4, H-8), 3.04 (1H, s, H-10), 4.35 (2H, brs, H-20), 5.58 (1H, d, J=4.2, H-7), 7.56 (1H, s, H-1).

$^{13}$C-NMR δc ($D_2O$): 162.4 (C-1), 135.0 (C-2), 211.5 (C-3), 74.4 (C-4), 37.2 (C-5), 135.7 (C-6), 132.8 (C-7), 39.0 (C-8), 77.3 (C-9), 56.4 (C-10), 36.2 (C-11), 31.6 (C-12), 62.8 (C-13), 30.9 (C-14), 24.1 (C-15), 22.1 (C-16), 15.0 (C-17), 18.1 (C-18), 9.7 (C-19), 70.2 (C-20), 176.0 (C-21), 20.8 (C-22), 176.2 (C-23), 30.7 (C-24), 32.3 (C-25), 181.1 (C-26).

6.3 Example 3

α-Aminosuccinate of Prostratin

2-Formamido-succinic anhydride (28 mg, 0.1 mmol) in 2 ml of dichloromethane was treated with 1,3-dicyclohexylcarbodiimide (DCC) (2 mmol) under stirring at room temperature for 2 hrs. A solution of prostratin (139 mg, 0.1 mmol) and DMAP (24 mg, 0.2 mmol) in $CH_2Cl_2$ was added and stirred under nitrogen over night. The precipitate was removed and the solvent evaporated to dryness. Compound was purified by preparative TLC to give pure product (Scheme (1), product 2).

6.4 Example 4

Solubility of Prostratin and SA-101B

Solubility of prostratin and SA-101B was measured in pH controlled solutions and in various representative formulations, in particular, intravenous formulations, where solubility is often a limiting factor.

With reference to the data presented in Table 1, SA-101B had a better solubility than prostratin in all media.

TABLE 1

| | Solubility (in mg/mL) | | | | | | |
|---|---|---|---|---|---|---|---|
| Compound # | pH 1 | pH 2 | pH 5 | pH 7.5 | pH 9 | 5% Dextrose | Saline (0.9% NaCl) |
| SA-101A | 0.37 | 0.37 | 0.45 | 0.42 | 0.39 | 0.33 | 0.34 |
| SA-101B | 1.21 | 4.46 | 7.72 | 11.20 | 12.08 | >10 | >10 |

6.5 Example 5

Antiviral Activity of SA-101B Against HIV-1 in Human Macrophages

SA-101A and SA-101B were tested for antiviral activity against HIV-1 virus in peripheral blood monocytes/macrophages. Monocytes/macrophages were derived from normal HIV-1 negative donors, and cultured under conditions which promote cell survival and HIV replication. Fresh human blood was obtained commercially from Biological Specialty Corporation (Colmar, Pa.). The low passage, monocytropic, clinical isolate HIV-1Ba-L (Subtype B, R5) was obtained from the NIAID AIDS Research and Reference Reagent Program. A pre-titered aliquot of HIV 1Ba-L was removed from the freezer (−80° C.) and thawed rapidly to room temperature in a biological safety cabinet immediately before use. Phytohemagglutinin (PHA-P) was obtained from Sigma (St. Louis, Mo.) and recombinant IL-2 was obtained from R&D Systems Inc. (Minneapolis, Minn.).

Compound preparation: Compounds SA-101A and SA-101B were in powder form and solubilized in DMSO prior to use. AZT (Sigma), solubilized in sterile $dH_2O$, was used as the positive antiviral control. The compounds were tested at a 100 µg/mL high-test concentration; AZT was tested at a 1,000 ηM high-test concentration. Compound SA-101B was tested in the presence of 40% human AB serum.

Monocyte isolation and culture. Peripheral blood monocytes were isolated from screened donors sero-negative for HIV and HBV. Cells were pelleted by low speed centrifugation and re-suspended in PBS to remove contaminating platelets. The leukophoresed blood was then diluted with Dulbecco's phosphate buffered saline (PBS) and layered over of Lymphocyte Separation Medium (LSM; Cellgro® by Mediatech, Inc.; density 1.078+/−0.002 g/ml; Cat. #85-072-CL) in a 50 mL centrifuge tube and then centrifuged. Banded PBMCs were gently aspirated from the interface and subsequently washed with PBS by low speed centrifugation. The cells were diluted to $4 \times 10^6$ cells per mL in DMEM without phenol red supplemented with 10% heat inactivated human pooled AB serum, 2 mM L-glutamine, 100 U/mL penicillin and 100 µg/mL streptomycin. Monocytes/macrophages were allowed to adhere to the interior 60 wells (100 µL/well) of a 96 well flat bottomed plate for 2 to 18 hours at 37° C., 5% $CO_2$. The exterior wells were filled with 200 µL of sterile DPBS to serve as a humidity barrier. Following adherence of cells, the cultures were washed with sterile DPBS to remove non-adherent cells (lymphocytes and contaminating RBCs). Subsequently, 200 µL of RPMI 1640 supplemented with 15% FBS, 2 mM L-glutamine, 100 U/mL penicillin and 100 µg/mL streptomycin was added to the wells. The plates were incubated at 37° C. in a humidified incubator with 5% $CO_2$. Culture medium was replaced once per week until use. Culture plates were used for anti-HIV evaluations between days 6 and 14 of incubation following initial isolation of the cells.

Anti-HIV efficacy evaluation in human monocyte/macrophages. Following 6 to 14 days in culture, the monocyte/macrophages cultures were washed 3 times to remove any non-adherent cells, and serially diluted test compounds were added followed by the addition of a pre-titered amount of HIV. Cultures were washed a final time by media removal 24 h post infection, fresh compound added and the cultures continued for an additional six days. Assays were performed using a standardized microtiter plate format developed by the Infectious Disease Research Department of Southern Research Institute. Each plate contains virus/cell control wells (cells plus virus), experimental wells (drug plus cells plus virus) and compound control wells (drug plus media without cells, necessary for MTS monitoring of cytotoxicity). Since HIV is not cytopathic to monocytes/macrophages, this allows the use of the same assay plate for both antiviral activity and cytotoxicity measurements. At assay termination, virus replication was measured by collecting cell-free supernatant samples, which were analyzed for HIV p24 antigen content using a commercially available p24 ELISA assay (Coulter). Following removal of supernatant samples, compound cytotoxicity was measured by addition of MTS to the plates for determination of cell viability. Wells were also examined microscopically and any abnormalities noted. The HIV reverse transcriptase inhibitor AZT was used as a positive control compound and run in parallel with each determination.

p24 Antigen ELISA. ELISA kits were purchased from Coulter Electronics, and detection of supernatant or cell-associated p24 antigen is performed according to the manufacturer's instructions. All p24 determinations were performed following serial dilution of the samples to ensure absorbances in the linear range of the standard p24 antigen curve. The standard curve is produced using manufacturer-supplied standards and instructions. Data were obtained by spectrophotometric analysis at 450 ηm using a Molecular Devices Vmax or SpectraMaxPlus plate reader. Final concentrations were calculated from the optical density values using the Molecular Devices SoftMax Pro software package and expressed in pg/ml p24 antigen.

MTS staining for macrophage viability to measure cytotoxicity. At assay termination, the assay plates were stained with the soluble tetrazolium-based dye MTS (CellTiter Reagent, Promega) to determine cell viability and quantify compound cytotoxicity. MTS is metabolized by the mitochondrial enzymes of metabolically active cells to yield a soluble formazan product, allowing the rapid quantitative analysis of cell viability and compound cytotoxicity. At termination of the assay, 20 µL of MTS reagent was added per well and the plates incubated for 4 hrs at 37° C. Adhesive plate sealers were used in place of the lids, the sealed plate was inverted several times to mix the soluble formazan product. Developed plates were read spectrophotometrically at 490/650 ηm with a Molecular Devices Vmax plate reader.

Results. Compounds SA-101A and SA-101B were evaluated for anti-HIV activity in human macrophage cultures using HIV-1 isolate Ba-L. SA-101B was used in the presence of 40% human AB serum. The results are summarized in Table 2.

Both compounds demonstrated activity against HIV-1Ba-L with $IC_{50}$ values of 0.11 µg/mL for SA-101A and 0.28 µg/mL for SA-101B. Both compounds also displayed some cytotoxicity with $TC_{50}$ values of 17.3 µg/mL and 21.0 µg/mL respectively.

The control compound AZT, used in the macrophage assay in parallel with the test compounds, yielded $IC_{50}$ values that fell within the acceptable ranges normally observed when performing antiviral assays. Macroscopic observation of the cells in each well of the microtiter plate confirmed the cytotoxicity results obtained following staining of the cells with the MTS metabolic dye.

TABLE 2

SA-101B vs. HIV-1$_{Ba-L}$ in Human Macrophages

| Compound | $IC_{90}$ | $IC_{50}$ | $TC_{50}$ | Therapeutic Index |
|---|---|---|---|---|
| Prostratin | 0.28 µg/mL | 0.11 µg/mL | 17.3 µg/mL | 156 |
| AZT | 123 nM | 9.30 nM | >1,000 nM | >108 |
| SA-101B 40% Human AB serum | 7.29 µg/mL | 0.28 µg/mL | 21.0 µg/mL | 74.8 |

6.6 Example 6

Antiviral Activity of SA-101A and SA-101B Against HIV-1 in Human PBMCs

Compounds SA-101A and SA-101B were tested for antiviral activity against HIV-1 in peripheral blood mononuclear cells (PBMC) acutely infected with the HIV-1 isolates. PBMCs were derived from normal HIV-1 negative donors, and cultured under conditions which promote cell survival and HIV replication. Fresh human blood was obtained commercially from Biological Specialty Corporation (Colmar, Pa.). The low passage clinical isolates HIV-1Ba-L, HIVIIIB, and SIVmac251 were from the NIAID AIDS Research and Reference Reagent Program. Immediately before use, pre-titered aliquot of the viruses were removed from storage in a freezer (−80° C.) and thawed rapidly to room temperature in a biological safety cabinet. Phytohemagglutinin (PHA-P) was obtained from Sigma (St. Louis, Mo.) and recombinant IL-2 was obtained from R&D Systems Inc. (Minneapolis, Minn.). Antiviral activity was tested from a high-test concentration of 100 µM or 100 µg/ml with nine ½-log serial dilutions of the compound to derive applicable $IC_{50}$ (concentration inhibition virus replication by 50%), $IC_{90}$ (concentration inhibition virus replication by 90%), $TC_{50}$ (concentration decreasing cell viability by 50%) and TI (therapeutic index: $TC_{50}/IC_{50}$) values.

Preparation of PMBC. Fresh Human PBMCs, Seronegative for HIV and HBV, were isolated from screened donors (Interstate Blood Bank, Inc. Memphis, Tenn.). Cells were pelleted/washed 2-3 times by low speed centrifugation and resuspensded in PBS to remove contaminating platelets. The leukophoresed blood was then diluted 1:1 with Dulbecco's Phosphate Buffered Saline (DPBS) and layered over 14 mL of Lymphocyte Separation Medium (LSM; Cellgro® by Mediatech, Inc.; density 1.078+/−0.002 g/ml; Cat. # 85-072-CL) in a 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by trypan blue exclusion and re-suspended at $1\times10^7$ cells/mL in RPMI 1640 supplemented with 15% Fetal Bovine Serum (FBS), and 2 mM L-glutamine, 4 µg/mL Phytohemagglutinin (PHA-P, Sigma). The cells were allowed to incubate for 48-72 hours at 37° C. After incubation, PBMCs were centrifuged and re-suspended in RPMI 1640 with 15% FBS, 2 mM L-glutamine, 100 U/mL penicillin, 100 µg/mL streptomycin, 10 µg/mL gentamycin, and 20 U/mL recombinant human IL-2 (R&D Systems, Inc). IL-2 is included in the culture medium to maintain the cell division initiated by the PHA mitogenic stimulation. PBMCs were maintained in this medium at a concentration of $1-2\times10^6$ cells/mL with biweekly medium changes until used in the assay protocol. Cells were kept in culture for a maximum of two weeks before being deemed too old for use in assays and discarded. Monocytes were depleted from the culture as the result of adherence to the tissue culture flask.

PMBC assay. For the standard PBMC assay, PHA-P stimulated cells from at least two normal donors were pooled (mixed together), diluted in fresh medium to a final concentration of $1\times10^6$ cells/mL, and plated in the interior wells of a 96 well round bottom microplate at 50 µL/well ($5\times10^4$ cells/well) in a standard format developed by the Infectious Disease Research department of Southern Research Institute. Pooling (mixing) of mononuclear cells from more than one donor is used to minimize the variability observed between individual donors, which results from quantitative and qualitative differences in HIV infection and overall response to the PHA and IL-2 of primary lymphocyte populations. Each plate contains virus/cell control wells (cells plus virus), experimental wells (drug plus cells plus virus) and compound control wells (drug plus media without cells, necessary for MTS monitoring of cytotoxicity). Since HIV-1 is not cytopathic to PBMCs, this allows the use of the same assay plate for both antiviral activity and cytotoxicity measurements. Test drug dilutions were prepared at a 2× concentration in microtiter tubes and 100 µL of each concentration was placed in appropriate wells using the standard format. 50 µL of a predetermined dilution of virus stock was placed in each test well (final MOI~0.1). The PBMC cultures were maintained for seven days following infection at 37° C., 5% $CO_2$. After this period, cell-free supernatant samples were collected for analysis of reverse transcriptase activity and/or HIV p24 content. Following removal of supernatant samples, compound cytotoxicity was measured by addition of MTS to the plates for determination of cell viability. Wells were also examined microscopically and any abnormalities were noted.

Reverse transcription activity assay. Reverse transcriptases activity measurements used the protocol described in Buckheit et al., 1991, *AIDS Research and Human Retroviruses* 7:295-302. Specifically, tritiated thymidine triphosphate ($^3$H-TTP, 80 Ci/mmol, NEN) was received in 1:1 $dH_2O$:Ethanol at 1 mCi/mL. Poly rA:oligo dT template:primer (Pharmacia) was prepared as a stock solution by combining 150 µL poly rA (20 mg/mL) with 0.5 mL oligo dT (20 units/mL) and 5.35 mL sterile $dH_2O$ followed by aliquoting (1.0 mL) and storage at −20° C. The RT reaction buffer was prepared fresh on a daily basis and consisted of 125 µL 1.0 M EGTA, 125 µL $dH_2O$, 125 µL 20% Triton×100, 50 µL 1.0 M Tris (pH 7.4), 50 µL 1.0 M DTT, and 40 µL 1.0 M $MgCl_2$. The final reaction mixture was prepared by combining 1 part $^3$H-TTP, 4 parts $dH_2O$, 2.5 parts poly rA:oligo dT stock and 2.5 parts reaction buffer. Ten microliters of this reaction mixture was placed in a round bottom microtiter plate and 15 µL of virus containing supernatant was added and mixed. The plate was incubated at 37° C. for 60 minutes. Following incubation, the reaction volume was spotted onto DE81 filter-mats (Wallac), washed 5 times for 5 minutes each in a 5% sodium phosphate buffer or 2×SSC (Life Technologies). Next they were washed 2 times for 1 minute each in distilled water, 2 times for 1 minute each in 70% ethanol, and then dried. Incorporated radioactivity (counts per minute, CPM) was quantified using standard liquid scintillation techniques.

p24 Antigen ELISA. ELISA kits are purchased from Coulter Electronics, and detection of supernatant p24 antigen is performed according to the manufacturer's instructions. All p24 determinations are performed following serial dilution of the samples to ensure absorbances in the linear range of the standard p24 antigen curve. The standard curve is produced using manufacturer-supplied standards and instructions. Data are obtained by spectrophotometric analysis at 450/570 ηm using a Molecular Devices Vmax or SpectraMaxPlus plate reader. Final concentrations are calculated from the optical density values using the Molecular Devices SoftMax Pro software package and expressed in pg/ml p24 antigen.

MTS staining for PBMC viability to measure cytotoxicity. At assay termination, assay plates were stained with the soluble tetrazolium-based dye MTS (CellTiter 96 Reagent, Promega) to determine cell viability and quantify compound toxicity. The mitochondrial enzymes of metabolically active cells metabolize MTS to yield a soluble formazan product.

This allows the rapid quantitative analysis of cell viability and compound cytotoxicity. The MTS is a stable solution that does not require preparation before use. At termination of the assay, 20 μL of MTS reagent was added per well. The microtiter plates were then incubated 4 6 hrs at 37° C. The incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 ηm with a Molecular Devices Vmax or SpectraMaxPlus plate reader.

Data analysis. Using an in-house computer program, $IC_{50}$ (50%, inhibition of virus replication), $IC_{90}$ (90%, inhibition of virus replication), $IC_{95}$ (95%, inhibition of virus replication), $TC_{50}$ (50% reduction in cell viability), $TC_{90}$ (90% reduction in cell viability), $TC_{95}$ (95% reduction in cell viability), and a therapeutic index ($TI=TC_{50}/IC_{50}$) were determined. AZT (nucleoside reverse transcriptase inhibitor) was used as a positive control antiviral compound.

Results. SA-101A and SA-101B were evaluated in a PBMC-based assay using the HIV-1 isolates Ba-L and IIIB and the SIV isolate mac251. SA-101B was tested against all three isolates in the presence of 40% human AB serum.

The preliminary results show that SA-101 A demonstrated activity against all three isolates evaluated in this study with $IC_{50}$ values ranging from 0.05 to 0.39 μg/mL. The therapeutic indices ranged from >2.54 to 20.1. There was no cytotoxicity associated with this compound at the concentrations evaluated.

The preliminary results also demonstrated activity of SA-101B against HIV-1Ba-L with an $IC_{50}$ value of 0.0007 μg/mL and displayed no cytotoxicity at the concentrations evaluated. In the evaluations of SA-101B against HIV-IIIB and SIVmac251, the preliminary data suggest that this compound did not achieve $IC_{50}$ values in the concentrations tested. Further evaluations of the compounds against the various viral isolates can be warranted under defined conditions

TABLE 3

SA-101A or SA-101B vs. HIV-1$_{Ba-L}$ in Human PBMCs

| Compound | $IC_{90}$ | $IC_{50}$ | $TC_{50}$ | Therapeutic Index |
|---|---|---|---|---|
| SA-101A (Prostratin) | 0.39 μg/mL | 0.05 μg/mL | >1.00 μg/mL | >20.1 |
| AZT | 499 nM | 4.66 nM | >1,000 nM | >215 |
| SA-101B 40% Human AB serum | >1.00 μg/mL | 0.0007 μg/mL | >1.00 μg/mL | >1,361 |
| AZT 40% Human AB serum | 23.9 nM | 0.38 nM | >1,000 nM | >2,625 |

TABLE 4

SA-101A or SA-101B vs. HIV-1$_{IIIB}$ in Human PBMCs

| Compound | $IC_{90}$ | $IC_{50}$ | $TC_{50}$ | Therapeutic Index |
|---|---|---|---|---|
| SA-101A (Prostratin) | 0.50 μg/mL | 0.09 μg/mL | >1.00 μg/mL | >11.1 |
| AZT | 58.3 nM | 4.53 nM | >1,000 nM | >221 |
| SA-101B 40% Human AB serum | >1.00 μg/mL | >1.00 μg/mL | >1.00 μg/mL | NA |
| AZT 40% Human AB serum | 74.3 nM | 2.01 nM | >1,000 nM | >499 |

NA = Not achieved

TABLE 5

SA-101A and SA-101B vs. SIVMac251 in Human PBMCs.

| Compound | $IC_{90}$ | $IC_{50}$ | $TC_{50}$ | Therapeutic Index |
|---|---|---|---|---|
| SA-101A (Prostratin) | 0.90 μg/mL | 0.39 μg/mL | >1.00 μg/mL | >2.54 |
| AZT | 474 nM | 11.9 nM | >1,000 nM | >84.2 |
| SA-101B 40% Human AB serum | >1.00 μg/mL | >1.00 μg/mL | >1.00 μg/mL | NA |
| AZT 40% Human AB serum | 86.7 nM | 6.07 nM | >1,000 nM | >165 |

NA = Not achieved that would efficiently generate the active form of the phorbol compounds.

The control compound AZT was used in the PBMC assay in parallel with the test compounds and yielded $IC_{50}$ values that fell within the acceptable ranges normally observed when performing antiviral assays. Macroscopic observation of the cells in each well of the microtiter plate confirmed the cytotoxicity results obtained following staining of the cells with the MTS metabolic dye.

6.7 Example 7

Evaluation of Compounds SA-101A and SA-101B for Anti-HIV-1 Efficacy in CEM-SS Cells Antiviral efficacy of SA-101A and SA-101B compounds were evaluated in an HIV 1 antiviral cytoprotection assay using CEM-SS cells and the laboratory adapted HIV 1IIIB virus strain.

Compound preparation. Compounds SA-101A and SA-101B were prepared in powder form and solubilized in DMSO and stored at −20° C. AZT (Sigma), solubilized in sterile $H_2O$, was used as a positive antiviral control and was stored at 4° C. The compounds were evaluated at a high test concentration of 500 µg/mL. AZT was run in parallel at a concentration of 500 nM.

Cell Preparation. CEM-SS cells were passaged in T-75 flasks prior to use in the antiviral assay. On the day preceding the assay, the cells were split 1:2 to assure they were in an exponential growth phase at the time of infection. Total cell and viability quantification was performed using a hemacytometer and trypan blue exclusion. Cell viability was greater than 95% for the cells to be utilized in the assay. The cells were resuspended at $5\times10^4$ cells/ml in tissue culture medium and added to the drug-containing microliter plates in a volume of 50 µl.

Virus Preparation. The virus used for these tests was the lymphocytropic virus strain HIV 1IIIB. This virus was obtained from the NIH AIDS Research and Reference Reagent Program and was grown in CEM SS cells for the production of stock virus pools. For each assay, a pre-titered aliquot of virus was removed from the freezer (−80° C.) and allowed to thaw slowly to room temperature in a biological safety cabinet. The virus was resuspended and diluted into tissue culture medium such that the amount of virus added to each well in a volume of 50 µl was the amount determined to give approximately 90% cell killing at 6 days post-infection. $TCID_{50}$ calculations by endpoint titration in CEM-SS cells indicated that the multiplicity of infection of these assays was approximately 0.01.

MTS Staining for Cell Viability. At assay termination, the assay plates were stained with the soluble tetrazolium-based dye MTS (Cell Titer Reagent Promega) to determine cell viability and quantify compound toxicity. At termination of the assay, 20 µL of MTS reagent was added per well. The microtiter plates were then incubated 4 6 hrs at 37° C. Adhesive plate sealers were used in place of the lids, the sealed plate was inverted several times to mix the soluble formazan product and the plate was read spectrophotometrically at 490/650 ηm with a Molecular Devices Vmax plate reader.

Data Analysis. Using an in-house computer program, $IC_{50}$ (50%, inhibition of virus replication), $IC_{95}$ (95%, inhibition of virus replication), $TC_{50}$ (50% reduction in cell viability), $TC_{95}$ (95% reduction in cell viability), and a therapeutic index ($TI=TC_{50}/IC_{50}$) were determined.

Results. The results of the assay are summarized in Table 6.

TABLE 6

Activity of Compounds SA-101A and SA-101B Against HIV-1$_{IIIB}$ in CEM-SS Cells

| Compound | $IC_{50}$ | $TC_{50}$ | Therapeutic Index |
|---|---|---|---|
| SA-101A | 0.086 µg/mL | >0.50 µg/mL | >5.83 |
| SA-101B | NA | >0.50 µg/mL | NA |
| AZT | 0.012 µM | >0.50 µM | >41.1 |
| AZT | 0.009 µM | >0.50 µM | >55.1 |

NA = Not achieved

SA-101A was active in this assay with an $IC_{50}$ value of 0.086 µg/mL and a therapeutic index of >5.83. This compound demonstrated no cytotoxicity at the concentrations evaluated in this assay.

SA-101B did not achieve an $IC_{50}$ value and was deemed inactive in this assay. This compound demonstrated no cytotoxicity at the concentrations evaluated in the assay.

The control compound AZT was evaluated in parallel with the test compounds and yielded $IC_{50}$ values that fell within the acceptable ranges normally observed when performing antiviral assays. Macroscopic observation of the cells in each well of the microtiter plate confirmed the cytotoxicity results obtained following staining of the cells with the MTS metabolic dye.

6.8 Example 8

HEPG2 2.2.15 Antiviral Assays: Effect on Hepatitis B (HBV) In Vitro

Compounds SA-101A and SA-101B were evaluated for effect on Hepatitis B Virus replications using a cell culture based HBV replication system.

Compound preparation. The compounds were prepared in powder form (~1 mg) and solubilized in DMSO prior to use. Compound 3TC was used as positive antiviral control.

HepG2 2.2.15 Antiviral Assay. The assay developed is similar to that described ion the literature (Korba et al., 1991, *Antiviral Res.* 15: 217-228; Korba et al., 1992, *Antiviral Res.* 19: 55-70) with the exception that viral DNA detection and quantification have been improved and simplified (Buckwold et al., 2004, *Antiviral Res.* 61(1): 57-62). Briefly, HepG2-2.2.15 cells are plated in 96-well microtiter plates. Only the interior wells are utilized to reduce "edge effects" observed during cell culture; the exterior wells are filled with complete medium to help minimize sample evaporation. After 16-24 hours the confluent monolayer of HepG2-2.2.15 cells is washed and the medium is replaced with complete medium containing various concentrations of a test compound in triplicate. 3TC is used as the positive control, while media alone is added to cells as a negative control (virus control, VC). Three days later the culture medium is replaced with fresh medium containing the appropriately diluted drug. Six days following the initial administration of the test compound, the cell culture supernatant is collected, treated with pronase and DNAse and then used in a real-time quantitative TaqMan PCR assay. The PCR-amplified HBV DNA is detected in real-time by monitoring increases in fluorescence signals that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($IC_{50}$). A dye uptake assay is then employed to measure cell viability which is used to calculate toxicity ($TC_{50}$). The therapeutic index (TI) is calculated as $TC_{50}/IC_{50}$.

Results. Compounds SA-101A and SA-101B did not achieve $EC_{50}$ values in this assay and thus appeared inactive for inhibiting HBV in the particular assay format. There was no cytotoxicity associated with these compounds at the concentrations evaluated.

6.9 Example 9

HCV RNA Replicon Antiviral Assays

Compounds SA-101A and SA-101B were evaluated for their effect on HCV RNA replicons using an in vitro HCV virus replication system.

Compound preparation. Compounds were prepared as a powder (~1 mg) and solubilized in DMSO. IFNα was used as a positive antiviral control.

HCV RNA replicon system. The assay for HCV replication employed cell line ET (luc-ubi-neo/ET), which is a human Huh7 hepatoma cell line that contains an HCV RNA replicon with a stable luciferase (Luc) reporter and three cell culture-adaptive mutations (Pietschmann et al., 2002, *J. Virol.* 76:4008-4021). The HCV RNA replicon contains the 5' end of HCV (with the HCV Internal Ribosome Entry Site (IRES) and the first few amino acids of the HCV core protein) which drives the production of a firefly luciferase (Luc), ubiquitin (Ubi), and neomycin phosphotransferase (NeoR) fusion protein. Ubiquitin cleavage releases the Luc and NeoR proteins. The EMCV IRES element controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The Luc reporter is used as an indirect measure of HCV replication. The activity of the Luc reporter is directly proportional to HCV RNA levels and positive control antiviral compounds behave comparably using either Luc or RNA endpoints.

Luciferase assay. The ET cell line is grown in Dulbecco's modified essential media (DMEM), 10% fetal bovine serum (FBS), 1% penicillin-streptomycin (pen-strep), 1% glutamine, 5 mg/ml G418 in a 5% $CO_2$ incubator at 37° C. All cell culture reagents are from Gibco Life Technologies. Cells are trypsinized (1% trypsin:EDTA) and plated out at $5\times10^3$ cells/well in white 96-well assay plates (Costar) dedicated to cell number (cytotoxicity) or antiviral activity (Luc) assessments. Drugs are added at five half-log concentrations each and the assay is run in DMEM, 5% FBS, 1% pen-strep, 1% glutamine. Human interferon alpha-2b (PBL Biolabs, New Brunswick, N.J.) is included in each run as a positive control compound. Cells are processed 72 hr post drug addition when the cells are still sub confluent. Compound $IC_{50}$ and $IC_{90}$ values (antiviral activity) are derived from plots of HCV RNA levels assessed as HCV RNA replicon-derived Luc activity versus drug concentration using Steady-Glo assay reagent (Promega), with Luc luminescence read on a 1450 Microbeta liquid scintillation and luminescence counter. Compound $TC_{50}$ and $TC_{90}$ values (cytotoxicity) are calculated from plots of cell number vs. drug concentration using data from the CytoTox-ONE cell proliferation assay (Promega); with fluorescence read using an Analyst HT fluorometer. The CytoTox-ONE assay is an assay of the number of live cells present. It involves lysing cells to release LDH which drives the conversion of resauzurin to the fluorescent resorufin. Compound selectivity indices (SI=TC/IC) $SI_{50}$ and $SI_{90}$ values are calculated from spreadsheets.

Results. Compound SA-101B was not active in the assay ($EC_{50}$ was not reached) and it did not display any appreciable cytotoxicity ($IC_{50}$ was not reached).

Compound SA-101A did not appear to be active or cytotoxic, but appeared to inhibit and later stimulate the cells to grow in a dose-dependent manner. Studies with lower concentration of the drug can be more informative since the lowest concentrations employed in the assay resulted in greater than 50% inhibition of HCV RNA replicon associated luciferase activity. As such, an $EC_{50}$ for this compound was not obtainable from the results.

The foregoing descriptions of specific embodiments of the present disclosure have been presented for purposes of illustration and description. They are not intended to be exhaustive or to limit the scope of the disclosure to the precise forms disclosed, and obviously many modifications and variations are possible in light of the above teaching.

All patents, patent applications, publications, and references cited herein are expressly incorporated by reference to the same extent as if each individual publication or patent application was specifically and individually indicated to be incorporated by reference.

What is claimed is:

1. A compound according to structural formula (I):

R—X—O—C(O)—R'  (I)

including salts and hydrates thereof, wherein:
R is a residue of a phorbol ester;
X is an alkylene chain containing from 1 to 12 carbon atoms;
R' is a moiety that either bears a permanent charge or that is ionizable at a pH in the range of about 2 to about 8;
the illustrated —X—O—C(O)—R' group is linked to the 6-carbon of R; and
the illustrated —X—O—C(O)—R' group hydrolyzes under biological conditions to yield a group of the formula —X—OH.

2. The compound of claim 1 in which X is methano (—$CH_2$—).

3. The compound of claim 1 in which R' is a group that comprises a carboxyl group or a salt thereof.

4. The compound of claim 3 in which R' comprises a carboxyl-substituted lower alkyl or a salt thereof.

5. The compound of claim 3 in which R' is a group of the formula —$(CH_2)_m$—C(O)OM, where M is hydrogen or a counter ion and m is an integer ranging from 1 to 4.

6. The compound of claim 3 in which R' further comprises an amino group.

7. The compound of claim 6 in which R' comprises an amino acid.

8. The compound of claim 7 in which R' is selected from —$(CH_2)_n$—CH[($CH_2)_n$—$NH_2$]—$(CH_2)_n$—C(O)OM and —$(CH_2)_n$—CH($NH_2$)—$(CH_2)_n$C(O)OM, wherein M is hydrogen or a counter ion, and each n is, independently of the others, an integer ranging from 0 to 4.

9. The compound of claim 1 in which R is a group of the formula —Y—Z, wherein:
Y is a branched or unbranched, saturated or unsaturated alkylene chain containing from 1 to 4 carbon atoms;
Z is selected from —C(O)OM, —$NR^bR^b$ and —$NR^cR^cR^c$;
M is hydrogen or a counter ion;
each $R^b$ is, independently of the other, selected from hydrogen, lower alkyl, lower hydroxyalkyl, lower alkoxyalkyl, and heteroalkyl, or, alternatively, two $R^b$ groups bonded to the same nitrogen atom may be taken together with the nitrogen atom to which they are bonded to form a 5- to 7-membered heteroatomic ring; and
each $R^c$ is, independently of the others, selected from lower alkyl, lower hydroxyalkyl, lower alkoxyalkyl, and heteroalkyl.

10. The compound of claim 9 which has one or more features selected from:
any alkyl group or moiety is a branched or unbranched alkanyl;
Y is an alkano;
each $R^b$ is, independently of the other, selected from hydrogen and lower alkanyl;
each $R^c$ is, independently of the others, selected from lower alkanyl; and
$NR^bR^b$ is selected from morpholinyl, N-morpholinyl, piperazinyl, 1-piperazinyl, 1-methyl-piperazinyl and 1-methyl-4-piperazinyl.

11. The compound of claim 9 in which Y is selected from methano, ethano, propano and butano.

12. The compound of claim 11 in which Z is —C(O)OM.

13. The compound of claim 11 in which Z is selected from dimethylamino, diethylamino, trimethylamino, triethylamino, and N-morpholinyl.

14. The compound of claim 1 in which R is selected from structures (R1) and (R2):

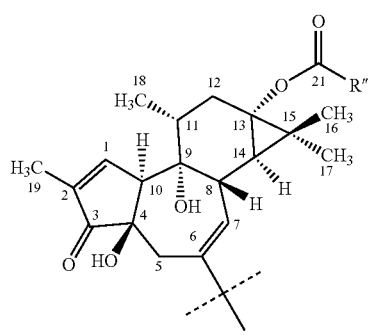
(R1)

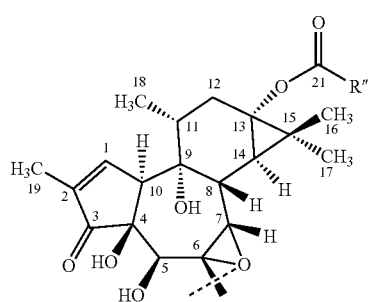
(R2)

wherein:
R″ is selected from $(C_1$-$C_{14})$ alkyl and benzyl.

15. The compound of claim 1 in which R is selected from structures (R1) and (R2):

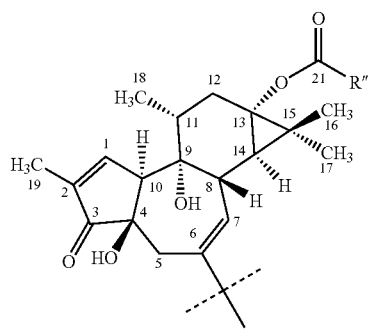
(R1)

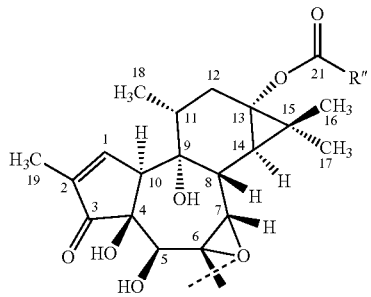
(R2)

wherein
R″ is selected from methyl, unsaturated lower alkyl, lower n-alkyl, benzyl, 4-hydroxybenzyl, 4-methoxybenzyl, and 4-acetyloxybenzyl.

16. The compound of claim 15 in which R' is a group that comprises a carboxyl group or a salt thereof.

17. The compound of claim 16 in which R' comprises a carboxyl-substituted lower alkyl or a salt thereof.

18. The compound of claim 16 in which R' is a group of the formula —$(CH_2)_m$—C(O)OM, where M is hydrogen or a counter ion and m is an integer ranging from 1 to 4.

19. The compound of claim 18 in which X is methano (—$CH_2$—).

20. The compound of claim 16 in which R' further comprises an amino group.

21. The compound of claim 20 in which R' comprises an amino acid.

22. The compound of claim 21 in which R' is selected from —$(CH_2)_n$—CH[$(CH_2)_n$—$NH_2$]—$(CH_2)_n$—C(O)OM and —$(CH_2)_n$—CH($NH_2$)—$(CH_2)_n$—C(O)OM, where M is hydrogen or a counter ion, and each n is, independently of the others, an integer ranging from 0 to 4.

23. The compound of claim 22 in which X is methano (—$CH_2$—).

24. The compound of claim 15 in which R is a group of the formula —Y—Z, wherein:
Y is a branched or unbranched, saturated or unsaturated alkylene chain containing from 1 to 4 carbon atoms;
Z is selected from —C(O)OM, —$NR^bR^b$ and —$NR^cR^cR^c$;
M is hydrogen or a counter ion;
each $R^b$ is, independently of the other, selected from hydrogen, lower alkyl, lower hydroxyalkyl, lower alkoxyalkyl, and heteroalkyl or, alternatively, two $R^b$ groups bonded to the same nitrogen atom may be taken together with the nitrogen atom to which they are bonded to form a 5- to 7-membered heteroatomic ring; and
each $R^c$ is, independently of the others, selected from lower alkyl, lower hydroxyalkyl, lower alkoxyalkyl, and heteroalkyl.

25. The compound of claim 24 which has one or more features selected from:
any alkyl group or moiety is a branched or unbranched alkanyl;
Y is an alkano;
each $R^b$ is, independently of the other, selected from hydrogen and lower alkanyl;
each $R^c$ is, independently of the others, selected from lower alkyanyl; and
$NR^bR^b$ is selected from morpholinyl, N-morpholinyl, piperazinyl, 1-piperazinyl, 1-methyl-piperazinyl and 1-methyl-4-piperazinyl.

26. The compound of claim 24 in which Y is selected from methano, ethano, propano and butano.

27. The compound of claim 24 in which Z is selected from dimethylamino, diethylamino, trimethylamino, triethylamino, and N-morpholinyl.

28. The compound of claim 24 in which the R" is selected from methyl, ethyl, propyl, butyl, pentyl, and benzyl.

29. The compound of claim 24 in which X is a methano (—$CH_2$—).

30. The compound of claim 1 which has the structure (Ia):

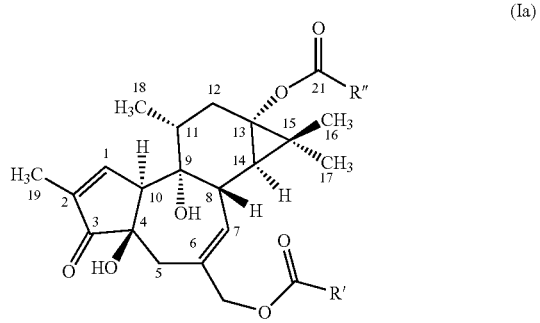

(Ia)

including the salts and hydrates thereof, wherein:
R" is selected from lower alkanyl, lower unsubstituted alkyl and benzyl.

31. The compound of claim 30 in which R is a group of the formula —Y—Z, wherein:
Y is a branched or unbranched, saturated or unsaturated alkylene chain containing from 1 to 4 carbon atoms;
Z is selected from —C(O)OM, —$NR^bR^b$ and —$NR^cR^cR^c$;
M is hydrogen or a counter ion;
each $R^b$ is, independently of the other, selected from hydrogen, lower alkyl, lower hydroxyalkyl, lower alkoxyalkyl, and heteroalkyl or, alternatively, two $R^b$ groups bonded to the same nitrogen atom may be taken together with the nitrogen atom to which they are bonded to form a 5- to 7-membered heteroatomic ring; and
each $R^c$ is, independently of the others, selected from lower alkyl, lower hydroxyalkyl, lower alkoxyalkyl, and heteroalkyl.

32. The compound of claim 31 which has one or more features selected from:
any alkyl group or moiety is a branched or unbranched alkanyl;
Y is an alkano;
each $R^b$ is, independently of the other, selected from hydrogen and lower alkanyl;
each $R^c$ is, independently of the others, selected from lower alkyanyl; and
$NR^bR^b$ is selected from morpholinyl, N-morpholinyl, piperazinyl, 1-piperazinyl, 1-methyl-piperazinyl and 1-methyl-4-piperazinyl.

33. The compound of claim 31 in which Y is selected from methano, ethano, propano and butano.

34. The compound of claim 33 in which Z is —C(O)OM.

35. The compound of claim 33 in which Z is selected from dimethylamino, diethylamino, trimethylamino, triethylamino, and N-morpholinyl.

36. The compound of claim 31 in which the R" is selected from methyl, ethyl, propyl, butyl, pentyl, and benzyl.

37. The compound of claim 31 in which R' is selected from —$(CH_2)_n$—CH[$(CH_2)_n$—$NH_2$]—$(CH_2)_n$—C(O)OM and —$(CH_2)_n$—CH($NH_2$)—$(CH_2)_n$—C(O)OM, where M is hydrogen or a counter ion, and each n is, independently of the others, an integer ranging from 0 to 4.

38. The compound of claim 1 which has the structure

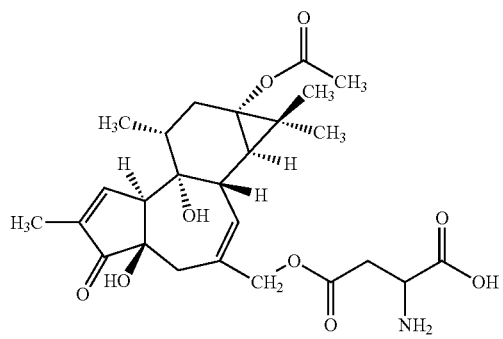

including the salts and hydrates thereof.

39. The compound of claim 1 which has the structure

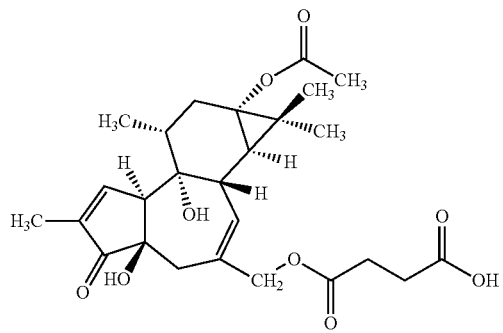

including the salts and hydrates thereof.

40. A pharmaceutical composition comprising a compound according to any one of claims 1-39, and a pharmaceutically acceptable excipient, diluent or carrier.

* * * * *